US007807668B2

(12) United States Patent
Denny et al.

(10) Patent No.: US 7,807,668 B2
(45) Date of Patent: Oct. 5, 2010

(54) ANTI-INFLAMMATORY COMPOUNDS

(75) Inventors: William Alexander Denny, Auckland (NZ); Brent Raymond Copp, Auckland (NZ); Allison Norrie Pearce, Auckland (NZ); Michael Vivian Berridge, Lower Hutt (NZ); Jacquie Lucille Harper, Lower Hutt (NZ); Nigel Brian Perry, Dunedin (NZ); Lesley Larsen, Dunedin (NZ); Colette Amirah Godfrey, Queensland (AU)

(73) Assignees: New Zealand Institute for Crop & Food Research Limited, Lincoln (NZ); National Institute of Water and Atmospheric Research Limited, Auckland (NZ); Malaghan Institute of Medical Research, Wellington (NZ)

(*) Notice: Subject to any disclaimer, the term of this patent is extended or adjusted under 35 U.S.C. 154(b) by 444 days.

(21) Appl. No.: 11/663,157

(22) PCT Filed: Sep. 16, 2005

(86) PCT No.: PCT/NZ2005/000246

§ 371 (c)(1),
(2), (4) Date: Jun. 25, 2007

(87) PCT Pub. No.: WO2006/031134

PCT Pub. Date: Mar. 23, 2006

(65) Prior Publication Data

US 2007/0265253 A1    Nov. 15, 2007

(30) Foreign Application Priority Data

Sep. 17, 2004  (NZ) ..................... 535383

(51) Int. Cl.
C07D 513/04    (2006.01)
A61K 31/5415  (2006.01)
A61K 31/542    (2006.01)
(52) U.S. Cl. .................. 514/224.2; 544/32; 544/34
(58) Field of Classification Search ............... 544/32, 544/34; 514/224.2
See application file for complete search history.

(56) References Cited

U.S. PATENT DOCUMENTS 3,040,041 A * 6/1962 Schellhammer ............... 544/32

OTHER PUBLICATIONS

Wolff, Manfred E. "Burger's Medicinal Chemistry and Drug Discovery, 5ed, vol. 1" John Wiley & Sons, 1995, pp. 975-977.*
Banker, G.S. et al, "Modern Pharmaceutices, 3ed." Marcel Dekker, New York, 1996, pp. 451 and 596.*
STN File CA, abstract 138:351250; & A. Aiello, et al; European Journal of Organic Chemistry (2003), 5, 898-900. See abstract and CAS Registry Nos. 519154-45-1 and 519154-46-2.
STN File CA, abstract 54:2182; & C.W. Schellhammer and S. Petersen, Ann. (1959), 624, 108-119. See abstract and CAS Registry No. 121761-11-3.
Aiello, A., et al; "Conicaquinones A and B, Two Novel Cytotoxic Terpene Quinones from the Mediterranean Ascidian *Aplidium conicum*"; *Eur. J. Org. Chem.*; pp. 898-900 (2003).
Townsend, N.O., et al; "Synthesis of 9-methyl-1*H*-[1,4]thiazino[3,2-g]quinoline-2,5,10(3*H*)-trione, the B,C,D ring core of the shermilamine alkaloids"; *Org. Biomol. Chem.*; pp. 3557-3563 (2003).
Schmitz, F.J., et al; "Xesto- and Halenaquinone Derivatives from a Sponge, *Adocia* sp., from Truk Lagoon[1]"; *J. Org. Chem.*; 53, pp. 3922-3925 (1988).
Schellhammer, C.W., et al; Uber Derivate Des Chinolinchinons-(5. 8); *Ann.*; 624, pp. 108-119 (1959).
Pearce, A. N., et al; "Anti-inflammatory Thiazine Alkaloids Isolated from the New Zealand Ascidian *Aplidium* sp.: Inhibitors of the Neutrophil Respiratory Burst in a Model of Gouty Arthritis"; *American Chemical Society and American Society of Pharmcognosy*; 5 pgs. (2006).

* cited by examiner

Primary Examiner—Kahsay T Habte
(74) Attorney, Agent, or Firm—Nixon & Vanderhye

(57) ABSTRACT

Compounds of formula (I) or formula (II) have anti-inflammatory activity and comprise a new class of NSAIDs. The compounds are useful for treating inflammatory diseases or disorders. The invention also provides pharmaceutical compositions containing these compounds, as well as methods of treating inflammatory diseases or disorders using compounds of formula (III) or formula (IV).

27 Claims, No Drawings

ANTI-INFLAMMATORY COMPOUNDS

This application is the U.S. National Phase of International Application PCT/NZ2005/000246, filed 16 Sep. 2005, which designated the U.S. PCT/NZ2005/000246 claims priority to New Zealand Application No. 535383 filed 17 Sep. 2004. The entire content of these applications are incorporated herein by reference.

TECHNICAL FIELD

The invention relates to anti-inflammatory compounds, compositions containing them and the use of such compounds in the treatment of inflammatory diseases.

BACKGROUND

Many people worldwide are affected by inflammatory diseases or disorders such as gout, acute or chronic idiopathic inflammatory arthritis, psoriasis, chronic dermatosis, myositis, demyelinating diseases, chronic obstructive pulmonary disease (COPD), interstitial lung disease, glomerulonephritis, interstitial nephritis, chronic active hepatitis, Crohn's disease, ulcerative colitis, plaque formation in atherosclerosis, degenerative diseases of the joints or nervous system, or multiple sclerosis (MS). Globally, populations are ageing and an increasing number of people require medication for age-related inflammatory diseases such as arthritis and gout. Similarly, there is an increase in the prevalence of allergic diseases such as asthma.

Steroids are one treatment option for inflammatory disorders such as asthma and arthritis. However, long term use of steroids gives rise to chronic side effects, including immunosuppression, tissue wasting and loss of bone density.

Another well-known class of anti-inflammatory pharmaceuticals is the non-steroidal anti-inflammatory drugs (NSAIDs). The primary mode of action of known NSAIDs is through inhibition of the COX enzyme, which results in the inhibition of prostaglandin synthesis. There are two different isoforms of the COX enzyme, COX-1 and COX-2. NSAIDs inhibit both isoforms to varying degrees.

The NSAIDs currently in the marketplace provide some alternative to steroid-based treatments. However, administration of NSAIDs can cause highly undesirable side effects such as gastro-intestinal bleeding, ulcers and renal disease. In certain cases, these drugs do not provide effective relief for some sufferers of inflammatory disease.

Thus, there is currently a need for new anti-inflammatory pharmaceuticals with reduced side effects.

As part of their search for new NSAIDs, the applicants have targeted a different part of the inflammatory cascade, seeking compounds that inhibit superoxide release by neutrophils and/or suppress neutrophil infiltration. This search has focussed on natural products as lead compounds.

The vast diversity of natural flora and fauna provides a large and varied source of natural product compounds with interesting structures and biological activities. Marine organisms, for example, can be a rich source of compounds, some of which possess surprising and useful activities.

Recently, interesting quinones have been isolated from ascidians. Compounds (A) and (B) were isolated from the Mediterranean ascidian *Aplidium conicum* (A. Aiello et al., *Eur. J. Org. Chem.*, 2003, 898).

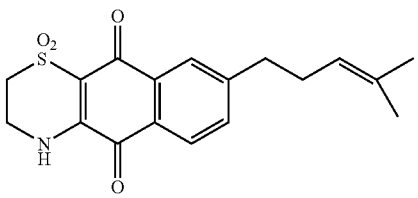

(A)

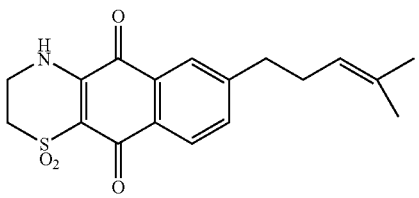

(B)

These compounds are of interest for their potential anti-cancer properties, and were found to be cytotoxic to rat glioma cells in vitro. However, they are not known to possess anti-inflammatory activity.

Synthetic quinoline-quinones are also known. Townsend and Jackson reported the synthesis of compound (C) in four steps from N-(4-bromo-2,5-dimethoxyphenyl)acetamide (N. O. Townsend and Y. A. Jackson, *Org. Biomol Chem.*, 2003, 1, 3557).

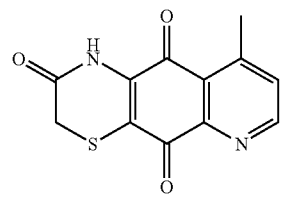

(C)

The compound was not reported to have any biological activity.

U.S. Pat. No. 3,040,041 discloses the synthesis of compounds (D), (E) and (F), which are tuberculostatic agents.

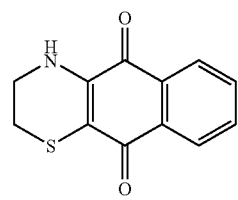

(D)

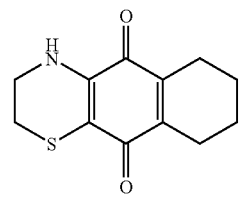

(E)

-continued (F)
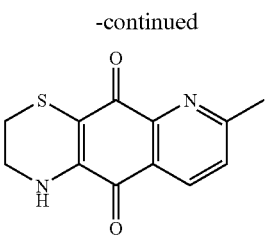

The synthesis of compound (G) from hypotaurine and naphthoquinone has been reported (F. J. Schmitz and S. J. Bloor, *J. Org. Chem.*, 1988, 53, 3922). The data reported by Schmitz and Bloor for the product isolated from the reaction of hypotaurine and naphthoquinone actually correspond to the quinone (H), but the structure was incorrectly reported as compound (G).

(G)
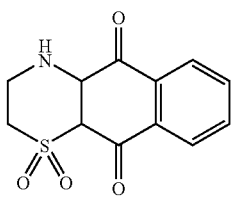

(H)
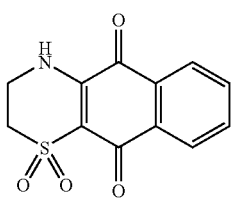

The isolated product (i.e. compound (H)) was found to be cytotoxic to lymphocytic leukemia cells in vitro.

Schelihammer et al. have reported the synthesis of compound (J) (C. W. Schellhammer and S. Petersen, Ann. (1959) 624, 108-119). This compound was found to have chemotherapeutic activity, but was not reported to have any anti-inflammatory activity.

(J)
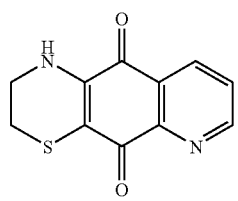

The applicants' research has led to the isolation of novel anti-inflammatory compounds from ascidians, in particular from an unnamed species (*Aplidium* sp. 15 ascidian). These compounds have provided a lead into the new class of anti-inflammatory compounds that is the subject of this application. The natural products and their synthetic derivatives and analogs form the basis of a new class of NSAIDs, with a different mode of action from known NSAIDs.

It is therefore an object of the invention to provide a novel class of anti-inflammatory compounds, or at least to provide a useful choice.

STATEMENTS OF INVENTION

In a first aspect, the invention provides a compound of formula (I)

(I)
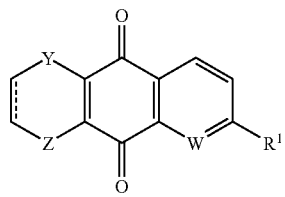

where: W is N, CH or COH;
Y is NH or $NR^2$ and Z is S, SO or $SO_2$, or
Z is NH or $NR^2$ and Y is S, SO or $SO_2$;
where $R^2$ is straight or branched chain $C_1$-$C_8$ alkyl;
$R^1$ is $CO_2H$, $CO_2R^3$, CHO, C(=O)$R^3$, CN, $CONH_2$, $CONHR^3$, $CON(R^3)_2$, $CH(OH)(OR^3)$, $CH(OR^3)_2$, H, halogen, $NHCOR^3$, $N(COR^3)_2$, $NH_2$, $NHR^3$, $N(R^3)_2$, $NO_2$, OH, $OR^3$, $SO_2NHR^3$, $SO_2N(R^3)_2$, $SO_3H$, $SO_2NH_2$, $SO_2R^3$, or
$R^1$ is straight or branched chain $C_1$-$C_8$ alkyl, $C_2$-$C_8$ alkenyl or $C_2$-$C_8$ alkynyl, each of which is optionally substituted with one or more substituents selected from aryl, heteroaryl, halogen, $NH_2$, $NHR^4$, $N(R^4)_2$, acyl, OH, $OR^4$, or phosphate, or
$R^1$ is a radical of formula (a), (b) or (c)

(a)
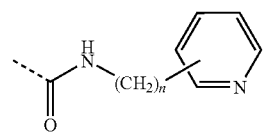

(b)
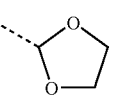

(c)
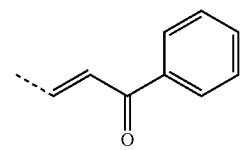

where n is an integer from 1 to 6;
where $R^3$ is straight or branched chain $C_1$-$C_8$ alkyl, $C_2$-$C_8$ alkenyl or $C_2$-$C_8$ alkynyl, aryl or heteroaryl group, optionally substituted with one or more substituents selected from halogen, $NH_2$, $NHR^4$, $N(R^4)_2$, OH, $OR^4$, acyl or phosphate;
and where $R^4$ is a straight or branched chain $C_1$-$C_8$ alkyl group, or where two $R^4$ groups together form a cyclopentyl, cyclohexyl, morpholyl, or N-methylpiperazinyl substituent;
------indicates a single bond or a double bond;
provided that the following compounds are excluded:
3,4-dihydro-2H-naphtho[2,3-b]-1,4-thiazine-5,10-dione;
2,3-dihydro-7-methyl-1H-pyrido[3,2-g][1,4]benzothiazine-5,10-dione;
2,3-dihydro-1H-pyrido[3,2-g][1,4]benzothiazine-5,10-dione;

3,4-dihydro-8-(4-methyl-3-pentenyl)-1,1-dioxide-2H-naphtho[2,3-b]-1,4-thiazine-5,10-dione;
3,4-dihydro-7-(4-methyl-3-pentenyl)-1,1-dioxide-2H-naphtho[2,3-b]-1,4-thiazine-5,10-dione;
3,4-dihydro-1,1-dioxide-2H-naphtho[2,3-b]-1,4-thiazine-5,10-dione;
or:
a compound of formula (II)

(II)

where: W, Y, Z and $R^1$ are as defined above;
$R^5$ is H, $C_1$-$C_8$ alkyl or acyl; and
------ indicates a single bond or a double bond;
or a pharmaceutically acceptable salt thereof, or a prodrug thereof.

Preferably the compound defined above is a compound of formula (I). Alternatively, the compound of the invention may be a compound of formula (II).

Preferably $R^1$ is straight or branched chain $C_1$-$C_8$ alkyl, $CO_2H$, $CO_2R^3$, CHO, CN, $CON(R^3)_2$, $COH(OR^3)$, H, or a radical of formula (a), (b) or (c).

More preferably $R^1$ is straight or branched chain $C_1$-$C_8$ alkyl, $CO_2H$, $CO_2R^3$, CN or $CON(R^3)_2$. It is further preferred that $R^1$ is straight or branched chain $C_1$-$C_8$ alkyl, still more preferably methyl.

Where $R^1$ is straight or branched chain $C_1$-$C_8$ alkyl, $R^1$ may be substituted with one or more $N(R^4)_2$ substituents where the two $R^4$ groups together form a morpholyl substituent.

Alternatively, $R^1$ may be $CON(R^3)_2$, preferably where $R^3$ is methyl. $R^1$ may also be $CO_2R^3$, preferably where $R^3$ is straight or branched chain $C_1$-$C_8$ alkyl, more preferably methyl. $R^1$ may also be $CO_2H$ or CN.

It is preferred that Y is NH or $NR^2$ and Z is S, SO or $SO_2$. Preferably Y is NH and Z is $SO_2$.

Alternatively it is preferred that Z is NH or $NR^2$ and Y is S, SO or $SO_2$. Preferably Z is NH and Y is $SO_2$.

It is preferred that W is N. Alternatively W may be CH or COH.

In a preferred embodiment of the invention, $R^1$ is $CO_2H$ or $CO_2R^3$, Z is NH and Y is S, SO or $SO_2$.

In another preferred embodiment $R^5$ is H.

In still another preferred embodiment of the invention W is N and $R^1$ is straight or branched chain $C_1$-$C_8$ alkyl or $CO(NR^3)_2$. Preferably $R^1$ is methyl. It is further preferred that $R^3$ is methyl.

Preferred compounds of the invention include:

(1)

-continued (2)

(3)

(4)

(5)

(6)

(7)

(8)

(9)

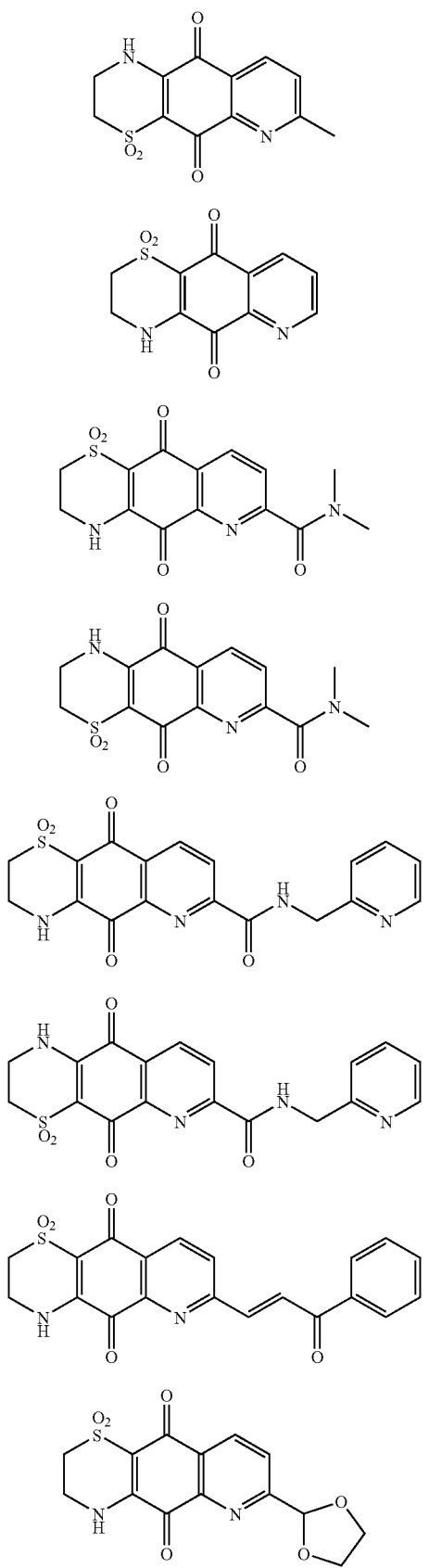

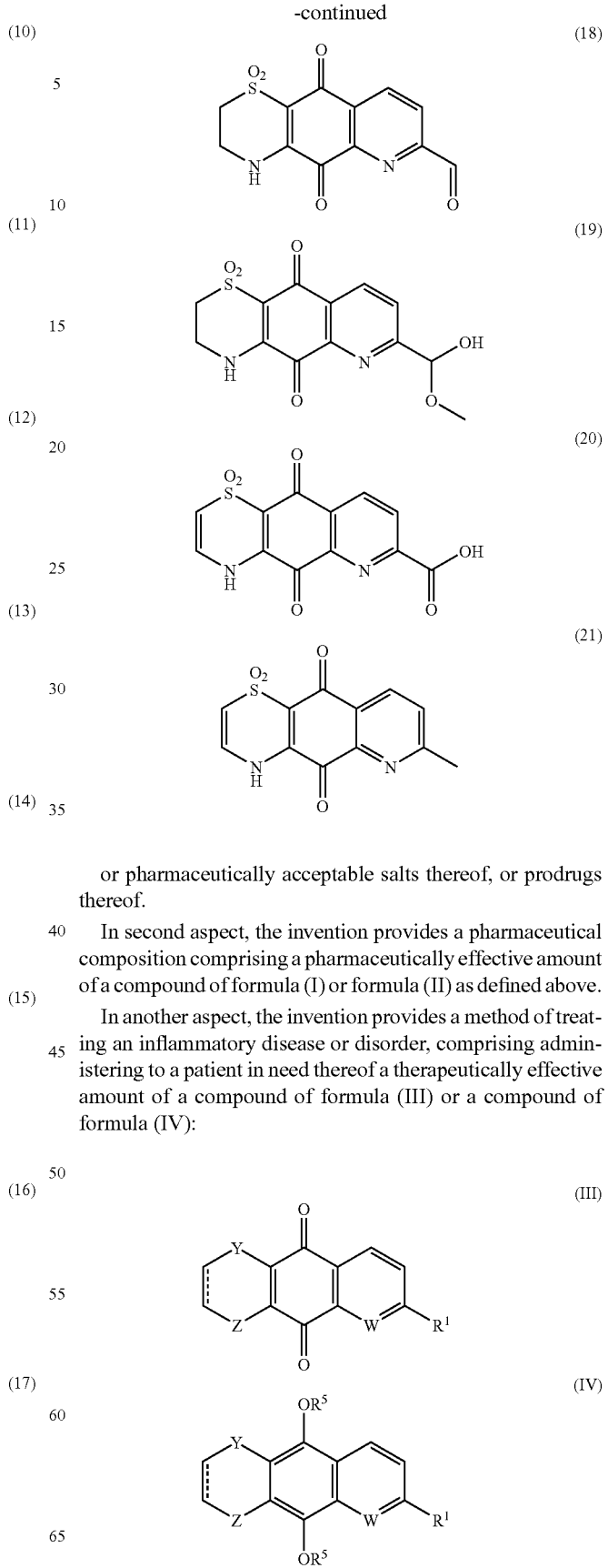

or pharmaceutically acceptable salts thereof, or prodrugs thereof.

In second aspect, the invention provides a pharmaceutical composition comprising a pharmaceutically effective amount of a compound of formula (I) or formula (II) as defined above.

In another aspect, the invention provides a method of treating an inflammatory disease or disorder, comprising administering to a patient in need thereof a therapeutically effective amount of a compound of formula (III) or a compound of formula (IV):

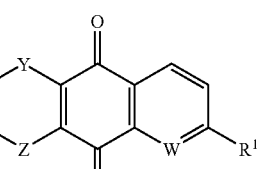

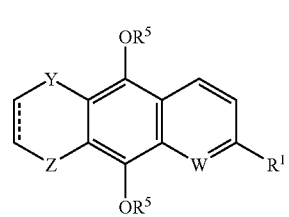

where: W, Y, Z, $R^1$ and $R^5$ are as defined above; and
═══indicates a single bond or a double bond;
or a pharmaceutically acceptable salt thereof, or a prodrug thereof.

Preferably the inflammatory disease or disorder is an inflammatory disease of the joints, skin, muscle, nervous system, lungs, kidneys, liver or gastrointestinal tract, or a disease in which inflammatory processes play a secondary role in the development of pathology or where inflammatory processes are involved in pathogenesis as a secondary phenomenon, such as vascular diseases, or an autoimmune disease where organ damage is mediated by inflammation.

More preferably the inflammatory disease or disorder is gout, acute or chronic idiopathic inflammatory arthritis, psoriasis, chronic dermatosis, myositis, a demyelinating disease, chronic obstructive pulmonary disease, interstitial lung disease, glomerulonephritis, interstitial nephritis, chronic active hepatitis, Crohn's disease, ulcerative colitis, plaque formation in atherosclerosis, a degenerative disease of the joints or nervous system, or multiple sclerosis.

DETAILED DESCRIPTION

Definitions

The term "pharmaceutically acceptable salts" as used herein is intended to apply to non-toxic salts with metal ions such as $Na^+$, $K^+$, $Ca^{2+}$, $Mg^{2+}$, $Zn^{2+}$, $Fe^{2+}$, $Fe^{3+}$ or with ammonia or organic amines.

The term "alkyl" is intended to include both straight- and branched-chain alkyl groups. Examples include: methyl group, ethyl group, n-propyl group, iso-propyl group, n-butyl group, iso-butyl group, sec-butyl group, t-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylpropyl group, heptyl group or octyl group. The terms "alkenyl" and "alkynyl" have corresponding meanings. Examples include vinyl group, allyl group, 1-propenyl group, 2-propenyl group, isopropenyl group, 2-methyl-1-propenyl group, 3-methyl-1-propenyl group, 2-methyl-2-propenyl group, 3-methyl-2-propenyl group, 1-butenyl group, 2-butenyl group, 3-butenyl group, 1-pentenyl group, 1-hexenyl group, 1,3-hexadienyl group, 1,6-hexadienyl group, heptenyl group, octenyl group, ethynyl group, 1-propynyl group, 2-propynyl group, 1-butynyl group, 2-butynyl group, 3-butynyl group, 3-methyl-1-propynyl group, 1,3-ethynyl-2-propynyl group, 2-methyl-3-propynyl group, 1-pentynyl group, 1-hexynyl group, 1,3-hexadiynyl group, 1,6-hexadiynyl group, heptynyl group or octynyl group.

The term "aryl" means an aromatic radical having 6 to 18 carbon atoms. Examples include monocyclic groups, as well as fused groups such as bicyclic groups and tricyclic groups. Suitable examples include phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, and benzocyclooctenyl group. The term "heteroaryl" means a heteroaromatic radical having 6 to 18 carbon atoms. Examples include pyridyl group, pyrrolyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, furyl group, pyranyl group, benzofuryl group, isobenzofuryl group, thiazolyl group, isothiazolyl group, benzothiazolyl group, oxazolyl group, and isoxazolyl group.

The term "acyl" as used herein means a radical having the formula RC(═O) where R is a $C_1$-$C_8$ alkyl group. Examples include acetyl group, propionyl group or butyroyl group.

The term "halogen" includes fluorine, chlorine, bromine and iodine.

The compounds are useful for the treatment of inflammatory diseases and disorders in humans and other animals. Thus, the term "patient" as used herein includes both human and other animal patients.

The term "prodrug" as used herein means a pharmacologically acceptable derivative of the compound of formula (I) or formula (II), such that an in vivo biotransformation of the derivative gives the compound as defined in formula (I) or formula (II). Prodrugs of compounds of formula (I) or formula (II) may be prepared by modifying functional groups present in the compounds in such a way that the modifications are cleaved in vivo to give the parent compound.

It will be appreciated by those skilled in the art that the quinone-type structure of formula (I) is related to the quinol-type structure of formula (II) via a 2-electron reduction. The reduced and oxidised forms are intimately related. For simplicity, the quinone and quinol structures are represented separately as formulae (I) and (II) (and as formulae (III) and (IV)) in the claims.

The Compounds of the Invention

The compounds of the invention exhibit anti-inflammatory activity, and comprise a new class of NSAIDs having a mode of action which involves inhibition of superoxide release by neutrophils and/or suppression of infiltration by neutrophils. The compounds therefore provide an alternative to known NSAIDs, many of which have undesirable side-effects.

Two examples of this new class are the natural products, compounds (1) and (2). The compounds of the invention also include derivatives and synthetic analogs of compounds (1) and (2), in particular compounds (3)-(22).

In the initial characterisation of the natural product (2), this compound was assigned the structure shown below, on the basis of NMR data.

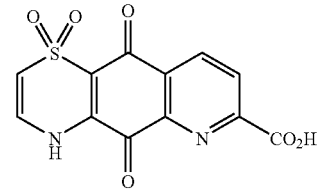

However, further analysis has since revealed that the correct structure is:

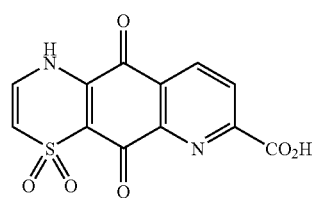

(2)

Example 1 describes the isolation of this natural product.

As noted above, the compounds of the invention form a new class of anti-inflammatory compounds whose mode of action involves inhibition of superoxide release by neutrophils and/or suppression of infiltration by neutrophils.

Table 2 (Example 3, below) shows the results of an in vitro respiratory burst assay for selected compounds of the invention. The anti-inflammatory data are expressed as $AI_{50}$, which corresponds to the concentration of compound required to reduce superoxide production in human neutrophils to 50% of controls. These data demonstrate that the compounds of the invention exhibit anti-inflammatory activity in vitro.

Furthermore, the compounds also exhibit anti-inflammatory activity in an in vivo mouse gout model. Table 3 (Example 4, below) shows that selected compounds of the invention, when administered orally, have a suppressive effect on the infiltration of neutrophils and/or on superoxide activity of neutrophils.

The compounds of the invention are therefore useful in the treatment of inflammatory diseases. Such diseases include inflammatory diseases of the joints, skin, muscle, nervous system, lungs, kidneys, liver or gastrointestinal tract, or diseases in which inflammatory processes play a secondary role in the development of pathology or where inflammatory processes are involved in pathogenesis as a secondary phenomenon, e.g. vascular diseases, or autoimmune diseases where organ damage is mediated by inflammation.

Examples of inflammatory diseases or disorders which the compounds may be used to treat include gout, acute or chronic idiopathic inflammatory arthritis, psoriasis, chronic dermatosis, myositis, a demyelinating disease, chronic obstructive pulmonary disease, interstitial lung disease, glomerulonephritis, interstitial nephritis, chronic active hepatitis, Crohn's disease, ulcerative colitis, plaque formation in atherosclerosis, degenerative diseases of the joints or nervous system, or multiple sclerosis.

Advantageously, the compounds act via a different mode of action from current commercially available NSAIDs— namely, the present compounds inhibit superoxide release by neutrophils and/or suppress neutrophil infiltration. The compounds may therefore avoid some of the side effects such as gastro-intestinal bleeding, ulcers and renal disease that are problematic with current NSAIDs. The compounds may be particularly useful for treating patients who are at risk from such side effects.

Synthesis of the Compounds of the Invention

Most of the synthetic analog and derivative compounds can be prepared from either commercially available, or readily prepared, 8-hydroxyquinolines (Scheme 1).

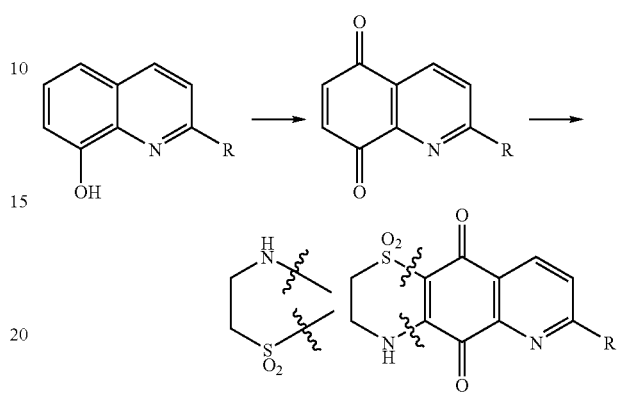

The 8-hydroxyquinolines are first oxidised using freshly prepared potassium nitrosodisulfonate (Fremy's salt) to their respective quinones, then hypotaurine is added by stirring a mixture of the two in a suitable solvent, such as aqueous acetonitrile solution, to give different proportions of the two regioisomers of the dioxothiazine ring. Due to the instability of the quinones, these are mostly used without purification in the hypotaurine addition reaction.

It was found in investigating the hypotaurine addition reactions that there was some evidence of the formation of small amounts of intermediates A and B (Scheme 2), but intermediate B in particular readily oxidised to the quinone during attempted purification procedures. The reduced, quinol forms C of the starting quinones were isolated from most reactions, showing that the quinone acts in part as an internal oxidizing agent.

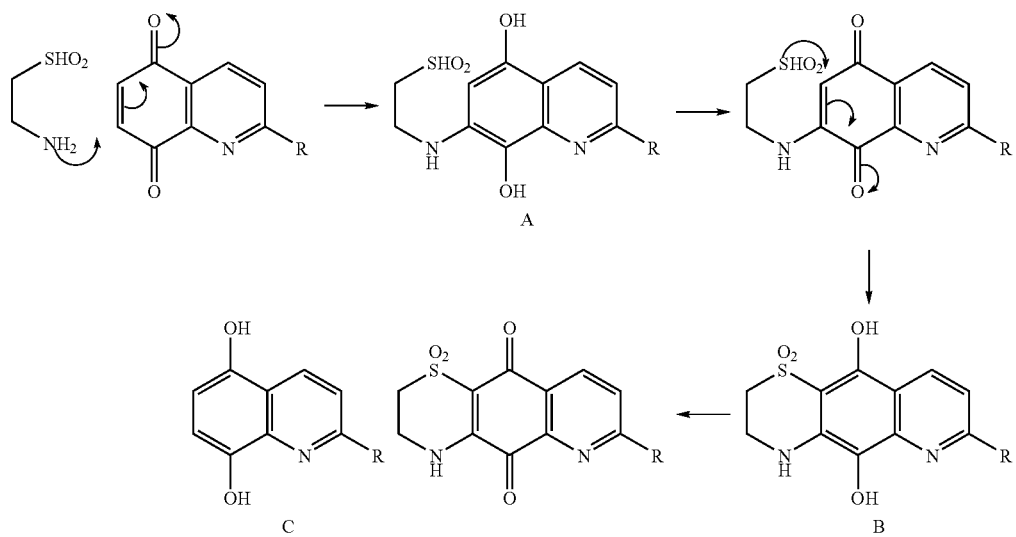

Other compounds can be prepared by modification of these hypotaurine adducts. Thus (18) can be prepared from a selenium dioxide oxidation of (9); and (19) can be prepared by treating (18) with methanol. Compound (21) is formed by treatment of (9) with aqueous potassium hydroxide solution (Scheme 3). Compound (20) can be formed in the same way from (1).

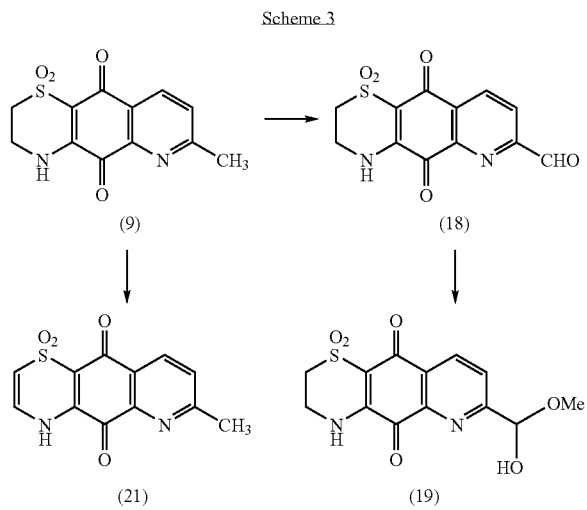

General Aspects

The compounds of the invention may be administered to a patient by a variety of routes, including orally, parenterally, by inhalation spray, topically, rectally, nasally, buccally or via an implanted reservoir. The amount of compound to be administered will vary widely according to the nature of the patient, the nature and extent of the disorder to be treated and the mode of administration. The dosage for, an adult human, for example, may be in the range less than 1 to 1000 milligrams, preferably 0.1 to 100 milligrams. The specific dosage required for any particular patient will depend upon a variety of factors, including the patient's age, body weight, general health, sex, species, the mode of administration, etc.

For oral administration the compounds can be formulated into solid or liquid preparations, for example tablets, capsules, powders, solutions, suspensions and dispersions. Such preparations are well known in the art as are other oral dosage regimes not listed here. In the tablet form the compounds may be tableted with conventional tablet bases such as lactose, sucrose and corn starch, together with a binder, a disintegration agent and a lubricant. The binder may be, for example, corn starch or gelatin, the disintegrating agent may be potato starch or alginic acid, and the lubricant may be magnesium stearate. For oral administration in the form of capsules, diluents such as lactose and dried cornstarch may be employed. Other components such as colorings, sweeteners or flavourings may be added.

When aqueous suspensions are required for oral use, the active ingredient may be combined with carriers such as water and ethanol, and emulsifying agents, suspending agents and/or surfactants may be used. Colourings, sweeteners or flavourings may also be added.

The compounds may also be administered by injection in a physiologically acceptable diluent such as water or saline. The diluent may comprise one or more other ingredients such as ethanol, propylene glycol, an oil or a pharmaceutically acceptable surfactant.

The compounds may also be administered topically. Carriers for topical administration of the compounds of include mineral oil, liquid petrolatum, white petrolatum, propylene glycol, polyoxyethylene, polyoxypropylene compound, emulsifying wax and water. The compounds may be present as ingredients in lotions or creams, for topical administration to skin or mucous membranes. Such creams may contain the active compounds suspended or dissolved in one or more pharmaceutically acceptable carriers. Suitable carriers include mineral oil, sorbitan monostearate, polysorbate 60, cetyl ester wax, cetearyl alcohol, 2-octyidodecanol, benzyl alcohol and water.

The compounds may further be administered by means of sustained release systems. For example, they may be incorporated into a slowly dissolving tablet or capsule.

EXAMPLES

The invention is further described with reference to the following examples. It is to be appreciated that the invention is not limited by these examples.

Taxonomic Description of Aplidium sp. 15

EXTERNAL APPEARANCE: The species forms erect lamellate colonies to 10 cm in maximum height and 1 cm thick. Colonies are sometimes attached to the substratum by a short stalk of similar circumference. Common cloacal apertures of 1-2 mm in diameter are evenly distributed throughout the test. Zooids are arranged in regular circular systems around slightly raised common cloacal apertures. Living specimens have an opaque brown colored test and zooids are not pigmented.

INTERNAL STRUCTURE: The zooids are small and delicate; thorax and abdomen are the same length and the post-abdomen is long and narrow. The whole zooid is 6-9 mm long, the thorax and abdomen making-up 1/3 of the total body length. Fine longitudinal muscles are on the thorax. The atrial aperture has a conspicuous stout, wide lappet, which is bifurcate at its distal end and appears separate from the atrial opening. The branchial aperture has six low indistinct lobes. The branchial sac contains 14 rows of stigmata. The stomach is large, has 4-5 folds, and is attached to the branchial sac by a long oesophagus. The ovary is situated directly below the gut loop and testis follicles form a single row down the posterior 1/3 of the post-abdomen.

REMARKS: Of the species with 4-5 stomach folds and circular zooid systems, *Aplidium* sp. 15 most closely resembles *Aplidium gilvum* (Millar, R. H. (1982). The marine fauna of New Zealand: Ascidiacea. New Zealand Oceanographic Memoir 85(114 pp)). However, the morphology of the colony (sandy stalk) transparent test, pointed branchial lobes and structure of the atrial lappet sets the two species apart. *Aplidium* sp. 15 has not been described in New Zealand and does not resemble any of the Australian *Aplidium* species described (Kott, P. (1992). The Australian ascidiacea III. *Aplousobranchia* (2). Memoirs of the Queensland Museum. 32(2): 375-620.), and therefore is most likely to be a new species endemic to New Zealand.

Example 1

Isolation of Compounds (1) and (2)

Frozen bodies of the orange-brown colored colonial ascidian of an *Aplidium* sp.1 5 were freeze-dried (25.4 g) and extracted with MeOH (6×100 mL) followed by $CH_2Cl_2$ (2×100 mL). The combined extracts were filtered and dried to produce 9.96 g of crude extract which was subjected to C18 reversed-phase flash column chromatography (water through to MeOH/TFA). The anti-inflammatory assay showed the activity to be concentrated in the water fraction. Repeated C18 chromatography (water through to 100%MeOH) was followed by gel permeation chromatography on Sephadex LH20. Compound (1) was isolated as a yellow powder (5.1 mg, 0.02% dry wt). Pure compound (2) tailed after (1) as a pink eluate (1.3 mg, 0.005% dry wt), which turned yellow upon drying.

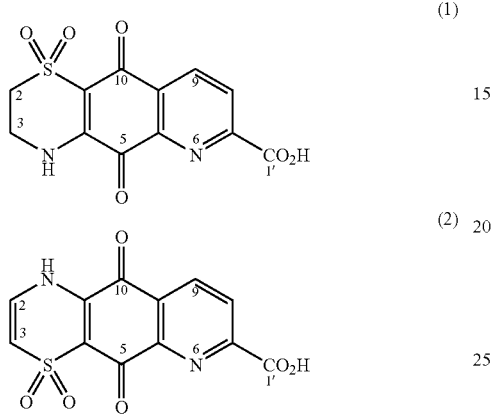

Compound (1): Yellow powder; IR (film) $v_{max}$ 3034, 1659, 1651,1585, 1417, 1193, 1129 cm$^{-1}$; UV (MeOH) $\lambda_{max}$ (log ε) 416 (3.40), 268 (4.21), 236 (4.46), 216 (4.37); (MeOH/TFA) 421 (3.56), 274 (4.18), 237 (4.55) 205 (4.43); (MeOH/KOH) 467 (3.59), 329 (3.97), 236 (4.52), 211 (5.07) nm; Fluorescence: (MeOH/TFA) Ex at 250 nm, Em 508 nm; (MeOH/KOH) Ex at 250 nm, Em 507 nm; Re-crystallized from water/MeOH/EtOH (1:2:10), small pink crystals, mp: slowly decomposes over 155° C.; $^1$H NMR (400 MHz, DMSO-d$_6$) δ 9.43 (1H, s, NH), 8.51 (1H, d, J=8.1 Hz, H-9), 8.38 (1H, d, J=8.1 Hz, H-8), 3.89 (2H, m, H$_2$-3), 3.41 (2H, t, J=6.0 Hz, H$_2$-2); $^{13}$C NMR in Table 1; HRFTMS (M–H)$^-$ m/z 307.0030, C$_{12}$H$_7$N$_2$O$_6$S requires 307.0025.

X-ray crystal analysis confirmed the structure.

Compound (2): Yellow powder; IR (film) $v_{max}$ 3414, 1681, 1638,1524,1279, 1127 cm$^{-1}$; UV (MeOH/TFA) $\lambda_{max}$ (log ε) 417 (3.11), 269 (3.91), 237 (4.02), 214 (4.50); (MeOH/KOH) 472 (3.29), 311 (3.62), 279 (3.81), 237 (4.04), 207 (4.95) nm. Fluorescence: (MeOH/TFA) Ex 250 nm, Em 505 nm; (MeOH/KOH) Ex 250 nm, Em 506 nm; $^1$H NMR (400 MHz, DMSO d$_6$) δ 8.45 (1H, d, J =7.9 Hz, H-9), 8.18 (1H, d, J=7.9 Hz, H-8), 7.34 (1H, d, J=7.9 Hz, H-2), 6.29 (1H, d, J=7.9 Hz, H-3); $^{13}$C NMR data in Table 1; HRFTMS (M–H)$^-$ m/z 304.9874, C$_{12}$H$_5$N$_2$O$_6$S requires 304.9868.

Example 2

Synthesis of Selected Compounds

General

All solvents were distilled before use and were removed by rotary evaporation at temperatures up to 35° C. Octadecyl functionalised silica gel (C18) was used for reversed-phase (RP) chromatography, and Merck silica gel 60, 200-400 mesh, 40-63 μm, was used for silica gel chromatography. TLC was carried out using Merck Silica gel 60 F254, first visualised with a UV lamp, and then by dipping in a vanillin solution (1% vanillin, 1% H$_2$SO$_4$ in EtOH), and heating. High resolution mass spectrometry was recorded using a VG70-250S double focussing magnetic sector mass spectrometer. UV spectra were recorded in methanol using a Jasco V-550. NMR spectra, at 25° C., were recorded at 500 or 300 MHz for $^1$H and 125 MHz or 75 MHz for $^{13}$C on Varian INOVA-500 or VXR-300 spectrometers. Chemical shifts are given in ppm on the δ scale referenced to the solvent peaks (CH$_3$)$_2$CO at 2.15 and (CD$_3$)$_2$CO at 30.5, or CH$_3$OD at 3.30 and CD$_3$OD at 49.0, (CH$_3$)$_2$SO at 2.62 and (CD$_3$)$_2$SO at 39.6.

HPLC

HPLC analyses were carried out using an Agilent HP1100 on a C18 column (Phenomenex Luna ODS(3) 5 μm 100 A 150×3 mm) at 20° C. with a 2×4 mm C18 guard column. Peaks were detected at 210 and 254 nm and UV spectra recorded from 190 to 600 nm. The mobile phase was acetonitrile in water, both with 0.1% formic acid: $t_0$=10% acetonitrile, $t_{12.5}$=100%, $t_{15}$=25%, $t_{16}$=10%, $t_{20}$10%. The flow rate was 0.5 mL/min, with an injection volume of 5 μL of 1 mg/ml solutions in methanol.

Example 2.1

Procedure for the Preparation of the Starting Materials

Typically a solution of Fremy's salt (1 g, 4 mmol) and potassium dihydrogenphosphate (400 mg, 3 mmol) in water (75 ml) was stirred at room temperature for 10 min then the quinolinol (6 mmol) in acetone (70 ml) was added. The mixture was stirred for 30 min, then a further solution of Fremy's salt (1 g) and potassium dihydrogenphosphate (400 mg) in water (30 ml) was added and the mixture stirred for 30 min, then a further solution of Fremy's salt (1 g) and potassium dihydrogenphosphate (400 mg) in water (30 ml) was added and the mixture stirred for a further 2 h. The mixture was extracted into dichloromethane, dried and evaporated in vacuo to give the product as an orange gum. Purification by column chromatography over silica gel eluting with ethyl acetate (0-40%) in dichloromethane gave the products as orange solids.

The following quinolines were prepared using this method:
5,8-Dihydro-5,8-dioxoquinoline (reg. no. 858471-89-3)
8-Hydroxyquinoline (1 g, 7 mmol) to give quinone (0.48 g, 44%).
2-Methyl-5,8-Dihydro-5,8-dioxoquinoline (reg. no. 90800-33-2)
2-Methyl-8-hydroxyquinoline (1 g, 6 mmol) to give quinone (0.45 g, 41%).
5,8-Dihydro-5,8-dioxoquinoline-2-carboxaldehyde (reg. no. 326801-24-5)
8-Hydroxyquinoline-2-carboxaldehyde (200 mg, 1.2 mmol) to give the quinone (160 mg, 74%).
5,8-Dihydro-5,8-dioxoquinoline-2-carbonitrile (reg. no. 326801-23-4)
8-Hydroxyquinoline-2-carbonitrile (1 g, 6 mmol) to give the quinone (0.25 g, 24%).
Methyl-5,8-dihydro-5,8-dioxoquinoline-2-carboxylate (reg. no. 326801-25-6)
Methyl-8-hydroxyquinoline-2-carboxylate (250 mg, 1.23 mmol) to give the quinone (220 mg, 82%).
5,8-Dihydro-5,8-dioxoquinoline-N,N-dimethyl-2-carboxamide.
8-Hydroxyquinoline-N,N-dimethyl-2-carboxamide (160 mg, 0.74 mmol) to give the quinone (140 mg, 82%).
5,8-Dihydro-5,8-dioxoquinoline-N-2-pyridylmethyl-2-carboxamide.

8-Hydroxy-N-((pyridin-2-yl)methyl)quinoline-2-carboxamide (110 mg, 0.4 mmol) to give the quinone (100 mg, 87%).

(E)-3-(5,8-Dihydro-5,8-dioxoquinolin -2-y)-I -phenyl-prop-2-en-1-one (E)-3-(8-hydroxyquinolin-2-yl)-1-phenylprop-2-en-1-one (60 mg, 0.22 mmol) to give the quinone (50 mg, 58%).

Also:

Preparation of Octyl-5,8-dihydro-5,8-dioxoquinoline-2-carboxylate

To a stirred solution of [bis(trifluoroacetoxy)iodo]benzene (PIFA) (258 mg, 0.6 mmol) in MeCN/water 2:1 (3 ml) at 0° C. was added octyl 8-hydroxyquinoline-2-carboxylate (71 mg, 0.24 mmol) in $CH_2Cl_2$ (1 ml). The solution was stirred for 20 min, poured into $CH_2Cl_2$ (20 mL), washed with water and dried in vacuo to give octyl 5,8-dioxo-5,8-dihydroquinoline-2-carboxylate (69 mg, 90%).

Example 2.2

Procedure for the Preparation of the Compounds of the Invention

Typically, a solution of hypotaurine (220 mg, 2 mmol) in water (4 ml) was added to the quinone (2.9 mmol) in acetonitrile (10 ml) and ethanol (10 ml). The reaction mixture was stirred at room temperature for 18 h, then the solvent was removed in vacuo to give an orange solid. Either isolation method 1 or isolation method 2 was employed.

Isolation method 1—Column chromatography on silica gel eluting with MeOH:chloroform (0:1 to 1:1) gave the product as an orange solid.

Isolation method 2—Methanol was added, the mixture sonicated for 1 min then the orange solid isolated by filtration, then washed with further methanol.

The following compounds were prepared using the above method:

Compound (3)

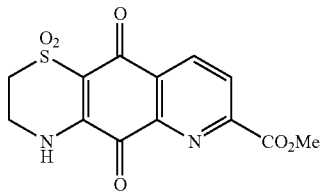

Compound (3)

Methyl-2H-pyrido[2,3-g][1,4]benzothiazine-5,10-dione, 3,4-dihydro-1,1-dioxo-7-carboxylate Quinone (220 mg, 1 mmol) with hypotaurine (120 mg) isolated by method 2 to give an orange solid (122 mg, 37%).

$^1$H NMR ($d_6$-DMSO) 9.46 (1H, s, NH), 8.54 (1H, d, J 8 Hz, H-9), 8.40 (1H, d, J 8 Hz, H-8), 3.95 (3H, s, $H_3$-1'), 3.89 (2H, m, $H_2$-3) and 3.38 (2H, m, $H_2$-2).

hu 13C NMR in Table 1.

UV (MeOH) $\lambda_{max}$ (log $\epsilon$) 408 (3.21), 269 (3.79), 236 (3.98) nm;

UV (MeOH+Acid) $\lambda_{max}$ (log $\epsilon$) 360 (3.11), 270 (4.09), 234 (3.99) nm;

UV (MeOH+Base) $\lambda_{max}$ (log $\epsilon$) 363 (3.59), 287 (3.73) nm; HPLC 5.18 min.

HRFABMS MH$^+$ m/z 323.0336 (calcd for $C_{13}H_{11}N_2O_6S$ 323.0338).

Compound (4)

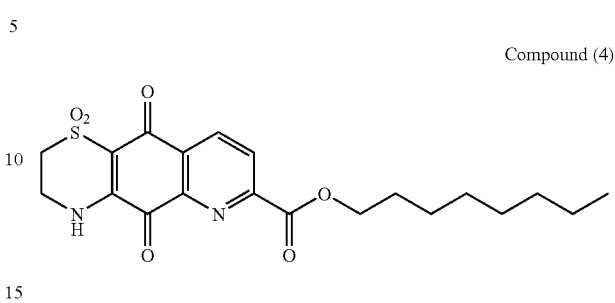

Compound (4)

Octyl-2H-pyrido[2,3-g][1,4]benzothiazine-5,10-dione, 3,4-dihydro-1,1-dioxo-7-carboxylate Quinone (140 mg) with hypotaurine (96 mg) isolated by method 1 to give a bright yellow solid (92 mg, 49%).

$^1$H NMR (d6-DMSO) 9.44 (1H, s, NH), 8.53 (1H, d, J 8 Hz, H-9), 8.39 (1H, d, J 8 Hz, H-8), 4.36 (2H, t, J 6.7 Hz, $H_2$-3'), 3.89 (2H, m, $H_2$-3), 3.41 (2H, t, J 6.0 Hz, $H_3$-10'). 1.75 (2H, m, $H_2$-4'), 1.40-1.26 (10H, m, $H_2$-5'-9'), 0.85 (3H, t, J 6.6 Hz, $H_3$-10').

$^{13}$C NMR in Table 1.

UV (MeOH) $\lambda_{max}$ (log $\epsilon$) 422 (3.19), 297 (3.70), 274 (3.76), 237 (4.10) nm.

IR (film)$\nu_{max}$ 3212, 2924, 2855, 1727, 1710, 1591,1463, 1346, 1285, 1166, 1122 cm$^{-1}$;

HRFABMS MH$^+$ m/z 421.1419; $C_{20}H_{25}N_2O_6S$ requires 421.1433.

Compound (5)

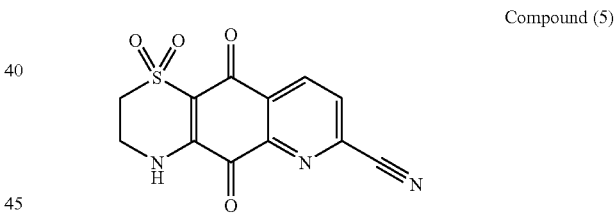

Compound (5)

2H-Pyrido[2, 3-g][1,4]benzothiazine-5,10-dione, 3,4-dihydro-1,1-dioxo-7-carbonitrile Quinone (200 mg, 1.1 mmol) with hypotaurine (80 mg) isolated by method 2 to give an orange solid (94 mg, 30%).

$^1$H NMR ($d_6$-Acetone) 8.78 (1H, d, J 8 Hz, H-9), 8.73 (1H, s, NH), 8.51 (1H, d, J 8 Hz, H-8), 4.27 (2H, m, $H_2$-3) and 3.52 (2H, m, $H_2$-2).

$^{13}$C NMR in Table 1.

UV (MeOH) $\lambda_{max}$ (log $\epsilon$) 397 (3.59), 273 (4.22), 232 (4.21) nm;

UV (MeOH+Acid) $\lambda_{max}$ (log $\epsilon$) 362 (3.50), 270 (4.52), 229 (4.24) nm;

UV (MeOH+Base) $\lambda_{max}$ (log $\epsilon$) 424 (3.68), 338 (3.86), 261 (4.23) nm;

HPLC 4.96 min.

HREIMS M$^+$ m/z 289.0152 (calcd for $C_{12}H_7N_3O_4S$, 289.0157).

Followed by Compound (6)

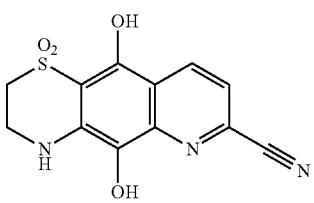

Compound (6)

2H-Pyrido[2,3-g][1,4]benzothiazine-5,10-dihydroxy, 3,4-dihydro-1,1-dioxo-7-carbonitrile as a brown solid (22 mg, 7%).

$^1$H NMR (d$_6$-DMSO) 8.87 (1H, d, J 8 Hz, H-9), 7.90 (1H, d, J 8 Hz, H-8), 7.80 (1H, s, NH), 3.69 (2H, m, H$_2$-3) and 3.27 (2H, m, H$_2$-2).

UV (MeOH) $\lambda_{max}$ (log $\epsilon$) 367 (3.50), 278 (4.11) nm;
UV (MeOH+acid) $\lambda_{max}$ (log $\epsilon$) 268 (4.26) nm;
UV (MeOH+base) $\lambda_{max}$ (log $\epsilon$) 279 (4.03) nm;
HPLC 5.05 min.

Compounds (7) major

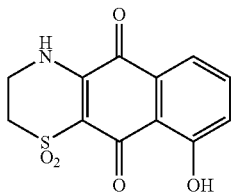

and (8) minor

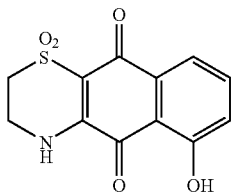

1H-Naphtho[3,2-b][1,4]thiazine-5,10-dione, 3,4-dihydro-6-hydroxy-1,1-dioxide and 2H-Naphtho[2,3-b][1,4]thiazine-5,10-dione, 3,4-dihydro-6-hydroxy-1,1-dioxide Juglone (80 mg) with hypotaurine (52 mg) isolated by method 1 gave a 2:1 inseparable mixture of regioisomers as an orange solid (62 mg, 48%).

$^1$H NMR (d6-DMSO) Major regioisomer: 12.94 (1H, s, OH), 9.61 (1H, s, NH), 7.75 (1H, dd, J 7,8 Hz, H-8), 7.67 (1H, dd, J 1,7 Hz, H-9), 7.45 (1H, dd, 1,8 Hz, H-7), 4.00 (2H, m, H$_2$-3) and 3.53 (2H, m, H$_2$-2).

Minor regioisomer: 11.32 (1H, s, OH), 9.28 (1H, s, NH), 7.88 (1H, dd, J 7,8 Hz, H-8), 7.63 (1H, dd, J 1,7 Hz, H-9), 7.37 (1H, dd, 1,8 Hz, H-7), 4.00 (2H, m, H$_2$-3) and 3.53 (2H, m, H$_2$-2).

$^{31}$C NMR in Table 1.

UV (MeOH) $\lambda_{max}$ (log $\epsilon$) 42 (3.72), 298 (3.92), 255 (4.18), 231 (4.23) nm;
UV (MeOH+acid) $\lambda_{max}$ (log $\epsilon$) 425 (3.72), 298 (3.92), 255 (4.18), 231 (4.23) nm;
UV (MeOH+base) $\lambda_{max}$ (log $\epsilon$) 468 (3.78), 273 (4.17), 242 (4.24) nm;
HPLC 7.6 min (major) and 6.8 min (minor)
HRESIMS MH$^+$ m/z 280.0277 (calcd for C$_{12}$H$_{10}$NO$_5$S, 280.0280).

Compound (9)

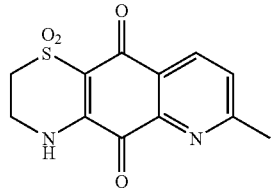

Compound (9)

2H-Pyrido[2,3-g][1,4]benzothiazine-5,10-dione, 3,4-dihydro-7-methyl-1,1-dioxide

Quinone (200 mg, 1.2 mmol) with hypotaurine (130 mg) isolated by method 1 gave an orange solid (50 mg, 16%)

$^1$H NMR (d$_6$-DMSO) 9.38 (1H, s, NH), 8.36 (1H, d, J 8 Hz, H-9), 7.84 (1H, d, J 8 Hz, H-8), 3.97 (2H, m, H$_2$-3), 3.51 (2H, m, H$_2$-2) and 2.75 (3H, s, H$_3$-1').

$^{13}$C NMR in Table 1.

UV (MeOH) $\lambda_{max}$ (log $\epsilon$) 423 (3.26), 291 (3.95), 266 (4.13), 234 (4.23) nm;
UV (MeOH+acid) $\lambda_{max}$ (log $\epsilon$) 426 (3.25), 294 (3.96), 266 (4.08), 258 (4.07), 234 (4.21) nm;
UV (MeOH+base) $\lambda_{max}$ (log $\epsilon$) 462 (3.42), 301 (3.97), 232 (4.26) nm;
HPLC 4.9 min.
HREIMS M$^+$ m/z 278.0352 (calcd for C$_{12}$H$_{10}$N$_2$O$_4$S, 278.0361).

X-ray crystal structure analysis confirmed the structure.

followed by Compound (10)

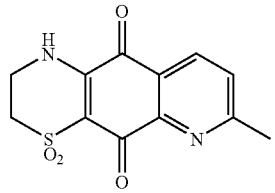

Compound (10)

1H-Pyrido[3,2-g][1,4]benzothiazine-5,10-dione, 2,3-dihydro-7-methyl-1,1-dioxide as a yellow solid (40 mg, 13%).

$^1$H NMR (d$_6$-DMSO) 9.29 (1H, s, NH), 8.37 (1H, d, J 8 Hz, H-9), 7.76 (1H, d, J 8 Hz, H-8), 3.98 (2H, m, H$_2$-3), 3.52 (2H, m, H$_2$-2) and 2.79 (3H, s, H$_3$-1').

$^{13}$C NMR in Table 1.

UV (MeOH) $\lambda_{max}$ (log $\epsilon$) 421(3.32), 293(4.04), 270(4.09), 235(4.28) nm;
UV (MeOH+Acid) $\lambda_{max}$ (log $\epsilon$) 429(3.45), 286(3.92), 273 (3.93), 231(4.23) nm;

UV (MeOH+Base) $\lambda_{max}$ (log ε) 450(3.48), 279(3.96), 231 (4.30) nm;
HPLC 5.3 min
HRESIMS m/z MH⁺ 279.0435 (calcd for $C_{12}H_{11}N_2O_4S$, 279.0440).

Compound (11)

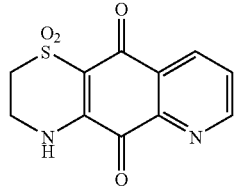

Compound (11)

2H-Pyrido[2,3-g][1,4]benzothiazine-5,10-dione, 3,4-dihydro-1,1-dioxide

Quinone (30 mg, 0.19 mmol) with hypotaurine (21 mg) isolated by method 2 gave an orange solid (20 mg, 40%).
¹H NMR (d₆-DMSO) 9.43 (1H, s, NH), 9.06 (1H, dd, J 1,3 Hz, H-9), 8.49 (1H, dd, J 1,6 Hz, H-7), 7.97 (1H, dd, J 3,6 Hz, H-8), 3.99 (2H, m, $H_2$-3) and 3.50 (2).
¹³C NMR in Table 1.
UV (MeOH) $\lambda_{max}$ (log ε) 421 (3.29), 265 (4.07), 232 (4.17) nm;
UV (MeOH+Acid) $\lambda_{max}$ (log ε) 421 (3.30), 265 (4.11), 231 (4.15) nm;
UV (MeOH+Base) $\lambda_{max}$ (log ε) 457 (3.44), 323 (3.79) nm;
HPLC 5.65 min.
HREIMS M⁺ m/z 264.0201 (calcd for $C_{11}H_8N_2O_4S$, 264.0205).

Compound (12)

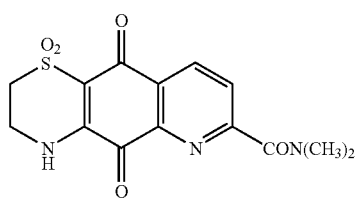

Compound (12)

2H-Pyrido[2,3-g][1,4]benzothiazine-5,10-dione, 3,4-dihydro-N,N-dimethyl-1,1-dioxo-7-carboxamide Quinone (140 mg, 0.61 mmol) with hypotaurine (90 mg) isolated by method 1 gave one regioisomer as an orange solid (52 mg, 26%)
¹H NMR (d₆-DMSO) 9.48 (1H, s, NH), 8.57 (1H, d, J 8 Hz, H-9), 8.07 (1H, d, J 8 Hz, H-8), 4.00 (2H, m, $H_2$-3), 3.51 (2H, m, $H_2$-2), 3.17 (3H, s, N-Me) and 3.04 (3H, s, N-Me).
¹³C NMR in Table 1.
UV (MeOH) $\lambda_{max}$ (log ε) 422 (3.02), 296 (3.65), 236 (3.96) nm;
UV (MeOH+Acid) $\lambda_{max}$ (log ε) 422 (3.02), 296 (3.65), 236 (3.96) nm;
UV (MeOH+Base) $\lambda_{max}$ (log ε) 462 (3.11), 335 (3.53) nm;
HPLC 4.48 min.

Followed by Compound (13)

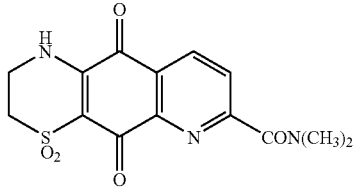

Compound (13)

1H-Pyrido[3,2-g][1,4]benzothiazine-5,10-dione, 2,3-dihydro-N,N-dimethyl-1,1-dioxo-7-carboxamide as an orange solid (15 mg, 8%)
¹H NMR (d₆-DMSO) 9.38 (1H, s, NH), 8.57 (1H, d, J 8 Hz, H-9), 7.99 (1H, d, J 8 Hz, H-8), 3.99 (2H, m, $H_2$-3), 3.52 (2H, m, $H_2$-2), 3.18 (3H, s, N-Me) and 3.04 (3H, s, N-Me). ¹³C NMR in Table 1.
UV (MeOH) $\lambda_{max}$ (log ε) 422 (3.29), 297 (3.94), 268 (4.01), 236 (4.21) nm;
UV (MeOH+Acid) $\lambda_{max}$ (log ε) 422 (3.29), 297 (3.94), 268 (4.02), 236 (4.21) nm;
UV (MeOH+Base) $\lambda_{max}$ (log ε) 459 (3.32), 333 (3.73), 257 (4.05) nm;
HPLC 4.21 min.
HRESIMS (M+Na)⁺ m/z 358.0474 (calcd for $C_{14}H_{13}N_3NaO_5S$, 358.0474).

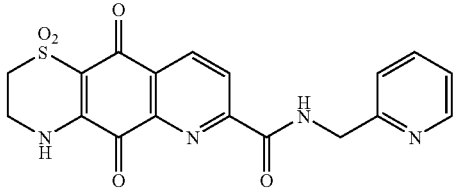

Compound (14)

and

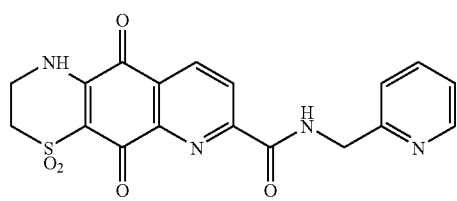

(15)

2H-Pyrido[2,3-g][1,4]benzothiazine-5,10-dione, 3,4-dihydro-N-((pyridin-2-yl)methyl)-1,1-dioxo-7-carboxamide Quinone (100 mg, 0.34 mmol) with hypotaurine (75 mg) isolated by method 1 gave an orange solid which was an inseparable 1:1 mixture of the two regioisomers (35 mg, 26%).
¹H NMR (d₆-DMSO) 9.42 (2H, m, NH), 8.67 (2H, m, H-9 and H-py), 8.56 (0.5H, d, J 8 Hz, H-8a), 8.46 (0.5H, d, J 8 Hz, H-8b), 7.91 (1H, m, H-py), 7.44 (1H, m, H-py), 7.40 (1H, m, H-py), 4.81 (2H, s, H-3'), 4.02 (2H, m, $H_2$-3) and 3.58 (2H, m, $H_2$-2).
$^{13}$C NMR in Table 1.
UV (MeOH) $\lambda_{max}$ (log ε) 421 (3.30), 262 (4.14), 238 (4.31) nm;
UV (MeOH+Acid) $\lambda_{max}$ (log ε) 420 (3.31), 266 (4.23), 238 (4.31) nm;
UV (MeOH+Base) $\lambda_{max}$ (log ε) 463 (3.43), 343 (3.87), 255 (4.30) nm;
HPLC 3.4 min and 3.0 min.
HREIMS M$^+$ m/z 398.0688 (calcd for $C_{18}H_{14}N_4O_5S$, 398.0685).

Compound (16)

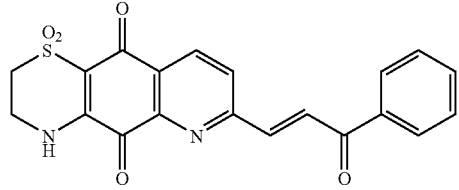

(E)-1-phenyl-3-(2H-Pyrido[2,3-g][1,4]benzothiazine-5,10-dione, 3,4-dihydro-1,1-dioxide)prop-2-en-1-one.

Quinone (50 mg, 0.17 mmol) with hypotaurine (30 mg) isolated by method 1 gave an orange solid (15 mg, 22%).
$^1$H NMR (d$_6$-DMSO) 9.35 (1H, s, NH), 8.46 (1H, d, J 8 Hz, H-9), 8.42 (1H, d, J 8 Hz, H-8), 8.26 (1H, d, J 16 Hz, H-2'), 8.14 (2H, d, J 7 Hz, H-5'), 7.80 (1H, d, J 16 Hz, 1'), 7.73 (1H, t, J 7 Hz, H-7'), 7.63 (2H, t, J 7 Hz, H-6'), 3.91 (2H, m, $H_2$-3) and 3.42 (2H, m, $H_2$-2).
$^{13}$C NMR in Table 1.
UV (MeOH) $\lambda_{max}$ (log ε) 313 (4.36), 274 (4.36), 244 (4.47) nm;
UV (MeOH+Acid) $\lambda_{max}$ (log ε) 421 (3.40), 313 (4.37), 274 (4.36), 244 (4.46) nm;
UV (MeOH+Base) $\lambda_{max}$ (log ε) 288 (4.42), 248 (4.54) nm;
HPLC 10.6 min.

Compound (17)

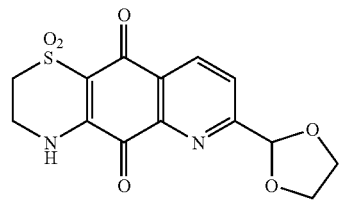

The quinone (10 mg, 0.043 mmol) with hypotaurine (9 mg) isolated by method 1 gave an adduct as an orange solid (frs 19-23, 1 mg).
$^1$H NMR (d6-acetone) 8.58 (1H, d, J 8 Hz, H-9), 8.11 (1H, d, J 8 Hz, H-8), 5.97 (1H, s, H-1'), 4.28 (2H, m, $H_2$-3), 4.16 (4H, m, $H_4$-3') and 3.53 (2H, m, $H_2$-2).
UV (MeOH) $\lambda_{max}$ (log ε) 421 (2.42), 267 (3.16), 233 (3.34) nm;
UV (MeOH+Acid) $\lambda_{max}$ (log ε) 411 (2.46), 267 (3.20), 232 (3.38) nm;
UV (MeOH+Base) $\lambda_{max}$ (log ε) 208 (4.52) nm;
HPLC 5.7 min.
HRESIMS (M+Na)$^+$ m/z 359.0313 (calcd for $C_{14}H_{12}N_2O_6SNa$ 359.0314).
Also:

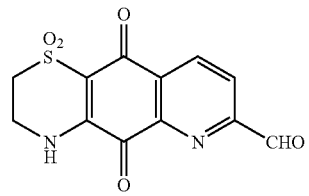

2H-Pyrido[2,3-g][1,4]benzothiazine-5,10-dione, 3,4-dihydro1,1-dioxo-7-carbaldehyde A stirred mixture of compound (9) (50 mg) and selenium dioxide (80 mg) in dioxane (4 ml) and water (0.5 ml) under $N_2$ was heated to 90° C. for 14 h, more selenium dioxide was added (80 mg) then the mixture heated to reflux for 4 h then more selenium dioxide was added (80 mg) and the mixture heated at reflux for a further 4 h. Separation by column chromatography over silica gel eluting with 10%-100% methanol in chloroform gave the aldehyde as an orange solid in fractions 20 to 27 (18 mg, 34%).
$^1$H NMR (d$_6$-DMSO) 10.23 (1H, s, CHO), 9.62 (1H, s, NH), 8.70 (1H, d, J 8 Hz, H-9), 8.40 (1H, d, J 8 Hz, H-8), 4.02 (2H, m, $H_2$-3) and 3.53 (2H, m, $H_2$).
$^3$C NMR in Table 1.
UV (MeOH) $\lambda_{max}$ (log ε) 421 (3.14), 289 (3.77), 267 (3.90), 234 (4.07) nm;
UV (MeOH+acid) $\lambda_{max}$ (log ε) 421 (3.15), 289 (3.78), 267 (3.90), 234 (4.08) nm;
UV (MeOH+base) $\lambda_{max}$ (log ε) 449 (3.60), 297 (3.92) nm;
HPLC 4.66 min.
HREIMS m/z M$^+$ 292.0147 (calcd for $C_{12}H_8N_2O_5S$, 292.0154).

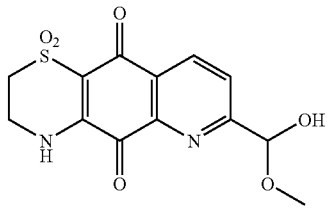

2H-Pyrido[2,3-g][1,4]benzothiazine-5,10-dione, 3,4-dihydro-1,1-dioxo-7-carbaldehyde A sample of compound (18) (5 mg) was left in methanol (1 ml) overnight then the solvents removed to give the hemi acetal (5 mg, 95%) as a yellow solid.
$^1$H NMR (CD$_3$OD) 8.53 (1H, d, J 8 Hz, H-9), 8.02 (1H, d, J 8 Hz, H-8), 5.64 (1H, s, H-1'), 4.04 (2H, m, $H_2$-3), 3.59 (3H, m, $H_4$-3') and 3.43 (2H, m, $H_2$-2).
UV (MeOH) $\lambda_{max}$ (log ε) 416 (2.95), 267 (3.72), 233 (3.91) nm;

UV (MeOH+Acid) λ$_{max}$ (log ε) 421 (2.94), 267 (3.74), 233 (3.91) nm;
UV (MeOH+Base) λ$_{max}$ (log ε) no maxima;
HPLC 4.65 min.
HRESIMS MH$^+$ m/z 325.0490 (calcd for C$_{13}$H$_{13}$N$_2$O$_6$S 325.0494).

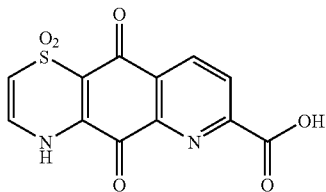

4H-Pyrido[2,3-g][1,4]benzothiazine-5,10-dione-1,1-dioxo-7-carboxylic acid

Compound (3) (87 mg) was stirred in 3N KOH (15 mL) at room temperature for 2 h.
Conc HCl was added dropwise until the reaction mixture turned acidic after which the solvents were removed under reduced pressure. The residue was taken up in water and subjected to reversed phase C18 flash chromatography to give the product as a bright yellow solid (13 mg, 16%).
$^1$H NMR (d$_6$-DMSO) 11.51 (1H, d, J 6 Hz, NH), 8.56 (1H, d, J 8 Hz, H-9), 8.41 (1H, d, J 8 Hz, H-8), 7.16 (1H, dd, J 6,9 Hz, H-3) and 6.61 (1H, d, J 9 Hz, H-2).
$^{13}$C NMR in Table 1.
UV (MeOH) λ$_{max}$ (log ε) 414 (3.55), 330 (3.77), 266 (4.26), 240 (4.35), 212 (4.42) nm; UV (MeOHITFA) λ$_{max}$ 424 (3.55), 268 (4.23), 213 (4.73) nm;
UV (MeOH/KOH) λ$_{max}$ 483 (3.78), 316 (3.99), 278 (4.19), 239 (4.45), 210 (5.04) nm;
Negative ionization ITMS m/z 305 (M–H)$^-$, HRFTMS m/z 304.9872; C$_{12}$H$_5$N$_2$O$_6$S requires 304.9868.

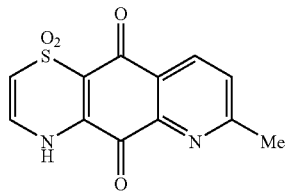

4H-Pyrido[2,3-g][1,4]benzothiazine-5,10-dione-7-methyl-1,1-dioxide

Compound (9) (10 mg, 0.036 mmol) was stirred in 1M KOH (2 ml) for 3 h. The initial orange red solid slowly went into solution over the 3 h. The resultant red orange solution was passed down a short column of weak cationic ion exchange resin (Amberlite IRC 86, 2 g) and a yellow solution was eluted. Water was washed through the resin until the eluent was colorless. The total eluent was freeze dried to give the pure product as a yellow solid (9 mg, 91%)
$^1$H NMR (d$_6$-DMSO) 8.41 (1H, d, J 8 Hz, H-9), 7.87 (1H, d, J 8 Hz, H-8), 7.26 (1H, d, J 9 Hz, H-3), 6.64 (1H, d, J 9 Hz, H-2) and 2.78 (3H, s, H$_3$-1').
$^{13}$C NMR in Table 1.

UV (MeOH) λ$_{max}$ (log ε) 421(3.09), 267(3.94), 238(3.97), 210(3.90) nm;
UV (MeOH+Acid) λ$_{max}$ (log ε) 421(3.09), 267(3.93), 238 (3.96);
UV (MeOH+Base) λ$_{max}$ (log ε) 479(3.49), 278(3.86), 235 (4.08) nm;
HPLC 4.11 min.
HREIMS M$^+$ m/z 276.0197 (calcd for C$_{12}$H$_8$N$_2$O$_4$S, 276.0205).

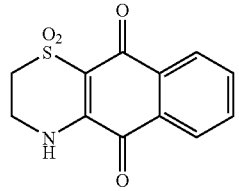

2H-Naphtho[2,3-b]-1,4-thiazine-5,10-dione, 3,4-dihydro-1,1-dioxide

Naphthoquinone (10 mg, 0.063 mmol) was dissolved in 1 mL of 1:1 ethanol/acetonitrile to which was added hypotaurine (7 mg, 0.065 mmol) dissolved in 0.5 mL water. The solution was heated at 105° C. for 10 min. A yellow product, 4, (4 mg, 24% yield) precipitated after cooling in an ice-bath for 5 min. IR: 3267, 1693, 1601, 1571, 1340, 1299, 1278, 1160, 1115 cm$^{-1}$; $^1$H NMR (300 MHz, d$_6$-DMSO) 9.12 (br s, 1H, NH), 8.01 (m, 2H, H-6, H-9), 7.93 (ddd, 1H, J 7.4, 7.4, 1.2 Hz, H-8), 7.81 (ddd, 1H, J 7.4, 7.4, 1.2 Hz, H-7), 3.86 (m, 2H, H-3), 3.38 (m, 2H, H-H-2); $^{13}$C NMR data in Table 1; FAB-MS: m/z 264 (M+H)$^+$, HRFAB-MS: m/z 264.0333; C$_{12}$H$_{10}$NO$_4$S requires 264.0331.
This compound has been synthesised previously (F. J. Schmitz and S. J. Bloor *J. Org. Chem.*, 1988, 53, 3922) and the above data match those reported. However, the structure was reported incorrectly by Schmitz and Bloor. The correct structure is that shown for compound (22).

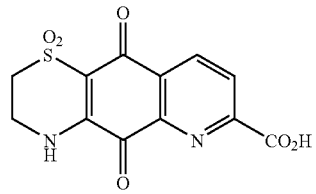

2H-Pyrido[2,3-g][1,4]benzothiazine-5,10-dione, 3,4-dihydr-1,1-dioxo-7-carboxylic acid Compound (3) (17 mg, 0.05 mmol) was dissolved in concd HCl (2 mL) and stirred for 5 h at room temperature, then at 100° C. for 1 h. The solution was dried under reduced pressure and subjected to C18 reversed-phase flash column chromatography. The product eluted with 6% MeOH/water as a bright yellow solid (11 mg, 68%).
Spectroscopic data matched the natural product, see above.

TABLE 1

$^{13}C$ NMR data for compounds 1-5, 7-12, 14-16, 18 and 20-22 (in $d_6$-DMSO except for compound 4 in $d_6$-acetone)

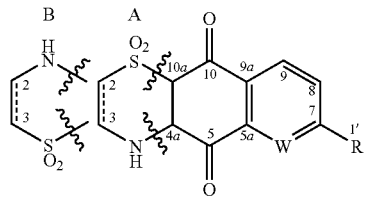

| Compound | 1 | 2 | 3 | 4 | 5 | 7* | 8* | 9 | 10 | 11 |
|---|---|---|---|---|---|---|---|---|---|---|
| R | CO2H | CO2H | CO2M | CO2Oct | CN | H | H | Me | Me | H |
| regio | A | B | A | A | A | B | A | A | B | A |
| 2-3 bond | — | = | — | — | — | — | — | — | — | — |
| W | N | N | N | N | N | COH | COH | N | N | N |
| Atom # | | | | | | | | | | |
| 2 | 48.1 | 141.8 | 47.7 | 48.1 | 50.3 | 39.7 | 48.4 | 48.3 | 39.7 | 48.3 |
| 3 | 39.0 | 114.1 | 39.0 | 39.0 | 41.5 | 48.4 | 39.7 | 39.6 | 48.4 | 39.9 |
| 4a | 147.7 | 113.9 | 147.3 | 147.8 | 148.7 | 110.1 | 147.0 | 147.2 | 112.1 | 147.5 |
| 5 | 176.2 | 176.5 | 175.7 | 176.1 | 177.8 | 181.5 | 181.6 | 177.1 | 173.3 | 177.0 |
| 5a | 146.2 | 147.3 | 145.9 | 146.4 | 148.5 | 113.8 | 114.5 | 145.7 | 146.5 | 146.4 |
| 6 | | | | | | 160.8 | 160.6 | | | |
| 7 | 151.3 | 158.2 | 149.4 | 150.1 | 137.8 | 125.9 | 122.5 | 162.7 | 165.4 | 153.3 |
| 8 | 128.9 | 126.0 | 128.7 | 129.1 | 134.8 | 135.0 | 138.2 | 128.8 | 126.7 | 134.0 |
| 9 | 135.6 | 137.0 | 135.4 | 135.8 | 137.9 | 119.2 | 118.1 | 134.2 | 134.6 | 129.1 |
| 9a | 131.5 | 127.8 | 131.4 | 131.7 | 133.7 | 130.3 | 133.0 | 127.9 | 125.3 | 130.0 |
| 10 | 173.2 | 181.1 | 172.7 | 173.2 | 174.2 | 177.9 | 174.1 | 174.3 | 178.8 | 174.1 |
| 10a | 110.7 | 150.8 | 110.3 | 110.7 | 114.0 | 147.9 | 111.2 | 110.3 | 147.3 | 110.6 |
| 1' | 165.1 | 165.8 | 163.7 | 163.6 | 117.9 | | | 24.4 | 24.9 | |
| 2' | | | 52.5 | 65.8 | | | | | | |
| 3' | | | | 31.2 | | | | | | |
| 4' | | | | 28.6 | | | | | | |
| 5' | | | | 28.6 | | | | | | |
| 6' | | | | 28.0 | | | | | | |
| 7' | | | | 25.3 | | | | | | |
| 8' | | | | 22.0 | | | | | | |
| 9' | | | | 13.9 | | | | | | |

| Compound | 12 | 14** | 15** | 16 | 18 | 20 | 21 | 22 |
|---|---|---|---|---|---|---|---|---|
| R | CONMe2 | CONHR | CONHR | eneone | CHO | CO2H | Me | H |
| regio | A | A | B | A | A | A | A | A |
| 2-3 bond | — | — | — | — | — | = | = | — |
| W | N | N | N | N | N | N | N | N |
| Atom # | | | | | | | | 13C |
| 2 | 48.3 | 48.3 | 39.5 | 48.3 | 48.3 | 112.0 | 111.8 | 48.2 |
| 3 | 39.6 | 39.5 | 48.4 | 39.5 | 39.5 | 130.4 | 131.5 | 39.0 |
| 4a | 147.6 | 147.0 | 112.7 | 146.6 | 147.9 | 141.5 | 140.5 | 148.7 |
| 5 | 176.6 | 176.3 | 172.5 | 176.6 | 176.3 | 175.5 | 175.8 | 178.7 |
| 5a | 145.4 | 145.6 | 147.8 | 147.6 | 146.9 | 146.5 | 145.8 | 129.9 |
| 6 | | | | | | | | 126.3 |
| 7 | 157.3 | 153.9 | 152.3 | 156.2 | 154.0 | 151.8 | 163.5 | 132.8 |
| 8 | 127.6 | 124.8 | 126.7 | 128.6 | 125.9 | 128.8 | 128.5 | 135.6 |
| 9 | 135.3 | 136.2 | 136.5 | 135.2 | 136.0 | 135.8 | 134.2 | 125.7 |
| 9a | 129.8 | 129.3 | 131.6 | 130.0 | 132.4 | 130.8 | 127.3 | 132.4 |
| 10 | 173.6 | 173.5 | 178.4 | 173.7 | 173.3 | 177.6 | 178.1 | 174.5 |
| 10a | 110.6 | 110.8 | 146.9 | 110.8 | 111.0 | 115.2 | 114.8 | 111.0 |
| 1' | 166.9 | 162.9 | 162.9 | 141.4 | 192.6 | 165.1 | 24.4 | |
| 2' | 38.2 | 44.5 | 44.5 | 128.0 | | | | |
| 3' | 34.9 | 157.6 | 157.5 | 189.5 | | | | |
| 4' | | 121.4 | 121.4 | 137.1 | | | | |
| 5' | | 136.9 | 136.9 | 128.4 | | | | |
| 6' | | 122.4 | 122.4 | 129.1 | | | | |
| 7' | | 149.0 | 149.0 | 133.7 | | | | |
| 8' | | | | | | | | |
| 9' | | | | | | | | |

*Data from a 2:1 mixture of compound 7: compound 8;
**Data from a 1:1 mixture of compound 14: compound 15

Example 3

In Vitro Studies in Respiratory Burst (Superoxide) Assay

Human neutrophils were isolated from anti-coagulated whole human blood using a Polymorphprep (density 1.13 g/mL, centrifuge 500×g, 40 min). Neutrophils were washed with PBS and plated out at 2×10$^6$ neutrophils per mL.

Neutrophils were treated with the compound (in DMSO) 30 minutes prior to addition of the detection dye WST-1 (5.5 mM). The respiratory burst was triggered by addition of PMA (200 ng/mL) and dye reduction was monitored (OD 450) for 25 minutes at 37° C.

Respiratory burst activity was calculated as the rate of dye reduction over time and was normalised to untreated cell controls. Anti-inflammatory activity is reported in Table 2 as the concentration required to reduce superoxide production to 50% of control, AI$_{50}$.

TABLE 2

In vitro Anti-inflammatory Activity of Compounds 1-22

| Compound | Structure | AI$_{50}$ (µM) |
|---|---|---|
| 1 | 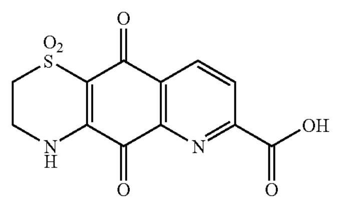 | 0.14 |
| 2 | 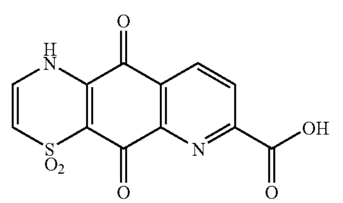 | 0.07 |
| 3 | 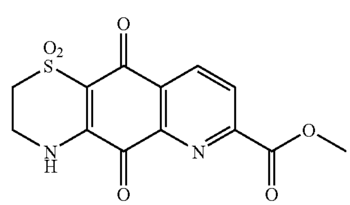 | 1.12 |
| 4 | 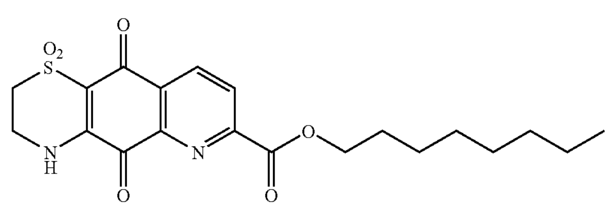 | 9.04 |
| 5 | 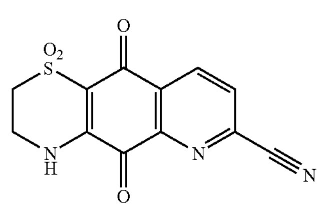 | 1.57 |
| 6 | 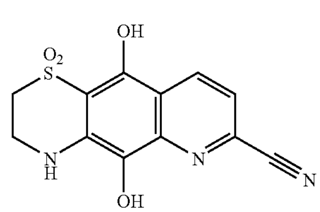 | 4.85 |

TABLE 2-continued

In vitro Anti-inflammatory Activity of Compounds 1-22

| Compound | Structure | AI$_{50}$ (μM) |
|---|---|---|
| 7 and 8, 2:1 mixture | (7), (8) | 8.27 |
| 9 | 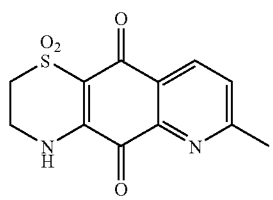 | >90 |
| 10 | 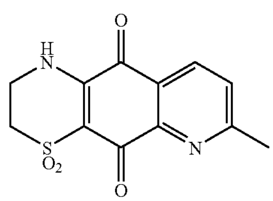 | >90 |
| 11 | 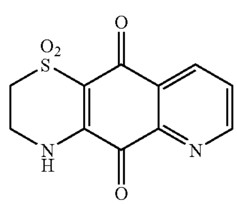 | 30 |
| 12 | 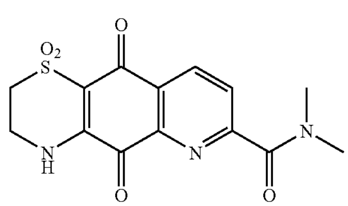 | 79 |
| 13 | 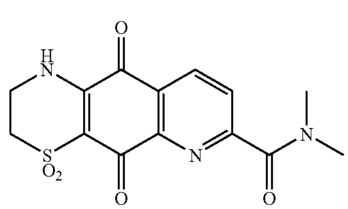 | 149 |

TABLE 2-continued

In vitro Anti-inflammatory Activity of Compounds 1-22

| Compound | Structure | AI$_{50}$ (μM) |
| --- | --- | --- |
| 14 and 15 1:1 mixture | | 2.31 |
| 16 | 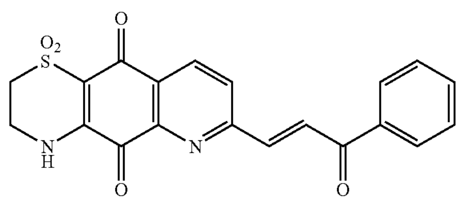 | 7.76 |
| 17 | 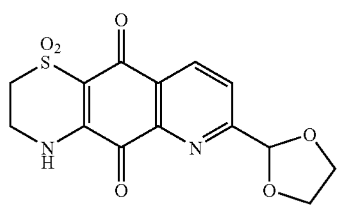 | >74 |
| 18 | 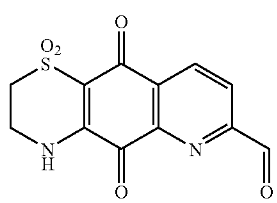 | 4.17 |
| 19 | 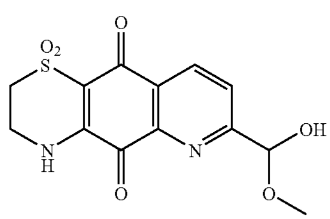 | 13 |
| 20 | 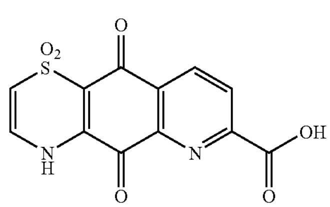 | 0.09 |

TABLE 2-continued

In vitro Anti-inflammatory Activity of Compounds 1-22

| Compound | Structure | AI$_{50}$ (µM) |
|---|---|---|
| 21 | [structure] | 8.93 |
| 22 | [structure] | >106 |

Example 4

In Vivo Studies in Mouse Gout Model (Monosodium Urate Crystal-Induced Murine Peritonitis)

Mouse Peritonitis was induced by intraperitoneal injection of 1 to 5 mg monosodium urate (MSU) crystals, in 0.5 µL PBS (0.1M, pH 7.4). Animals were treated with the compound(s) (in 250 µL PBS orally) at the doses indicated immediately prior to administration of the MSU crystals. 4 hours post administration, animals were euthanased by $CO_2$ exposure. The peritoneal cavity was washed with 3 mL of PBS containing 3 mM EDTA and 25 U/mL of heparin. The total cells in the lavage fluid were counted and an appropriate volume retained for H and E staining for differential counting (Getting et al. Molecular Determinants of Monosodium Urate Crystal—induced Murine Peritonitis: A role for Endogenous Mast Cells and a Distinct Requirement for Endothelial-derived Selectins. *J. Pharmacology and Experimental Therapeutics* 1997, 283: 123-30).

Treatment groups were as follows:
Oral Treatment
Untreated Control (Naive)
PBS Control (PBS oral+MSU crystals)
Colchicine+MSU crystals
Compound(s),(oral)+MSU crystals Results are shown in Table 3, which shows suppressive effects of oral administration of 25.6 µmol/kg of compounds 1-3, 5, 7-12, 14-16, 18, 21 and 22 on neutrophil infiltration (measured by total neutrophils per mL) and/or superoxide activity of neutrophils in the peritoneal wash.

TABLE 3

In vivo Anti-inflammatory Activity of Compounds 1-3, 5, 7-12, 16, 18, 21 and 22

| | | % suppression (25.6 mmol/kg, oral) | |
|---|---|---|---|
| Compound | Structure | Neutrophil infiltration | Superoxide production |
| 1 and 2, 9:1 mixture | [structure] | 35 | 60 |

TABLE 3-continued

In vivo Anti-inflammatory Activity of Compounds 1-3, 5, 7-12, 16, 18, 21 and 22

| Compound | Structure | % suppression (25.6 mmol/kg, oral) | |
|---|---|---|---|
| | | Neutrophil infiltration | Superoxide production |
| 3 | | — | 80 |
| 5 | | 25 | 50 |
| 7 and 8, 2:1 mixture | | 5 | 25 |
| 9 | | 50 | 80 |
| 10 | | 30 | 40 |
| 11 | | 30 | 20 |
| 12 | | 65 | 85 |

TABLE 3-continued

In vivo Anti-inflammatory Activity of Compounds 1-3, 5, 7-12, 16, 18, 21 and 22

| Compound | Structure | % suppression (25.6 mmol/kg, oral) | |
|---|---|---|---|
| | | Neutrophil infiltration | Superoxide production |
| 16 | 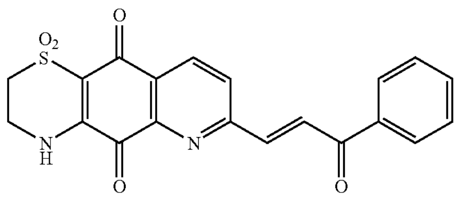 | 30 | 65 |
| 18 | 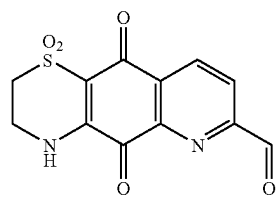 | — | 40 |
| 21 | 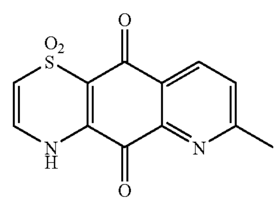 | 30 | 40 |
| 22 | 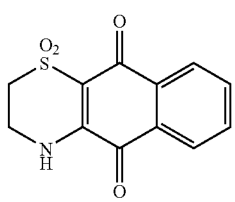 | 25 | 80 |

Although the invention has been described by way of example, it should be appreciated that variations or modifications may be made without departing from the scope of the invention. Furthermore, when known equivalents exist to specific features, such equivalents are incorporated as if specifically referred to in the specification.

INDUSTRIAL APPLICABILITY

The invention relates to anti-inflammatory compounds which comprise a new class of NSAIDs that may avoid some of the side effects of known NSAIDs. The compounds are therefore useful in treating inflammatory diseases or disorders.

The invention claimed is:
1. A compound of formula (I)

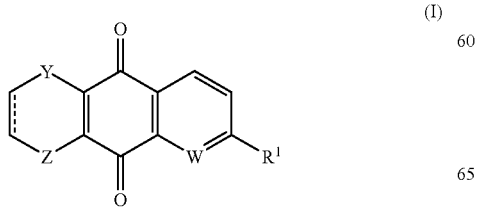

where: W is N,
Y is NH or $NR^2$ and Z is SO or $SO_2$ or
Z is NH or $NR^2$ and Y is S, SO or $SO_2$
where $R^2$ is straight or branched chain $C_1$-$C_6$ alkyl;
$R^1$ is $CO_2H$, $CO_2R^2$, CHO, C(=O)$R^3$, CN, $CONH_2$, $CONHR^3$, $CON(R^3)_2$, $CH(OH)(OR^3)$, $CH(OR^3)_2$, H, halogen, $NHCOR^3$, $N(COR^3)_2$, $NH_2$, $NHR^3$, $N(R^3)_2$, $NO_2$, OH, $OR^3$, $SO_2NHR^3$, $SO_2N(R^3)_2$, $SO_3H$, $SO_2NH_2SO_2R^3$, or
$R^1$ is straight or branched chain $C_1$-$C_8$ alkyl, $C_2$-$C_8$ alkenyl or $C_2$-$C_8$ alkynyl, each of which is optionally substituted with one or more substituents selected from aryl, heteroaryl, halogen, $NH_2$, $NHR^4$, $N(R^4)_2$, acyl, OH, $OR^4$, or phosphate, or $R^1$ is a radical of formula (a), (b) or (c)

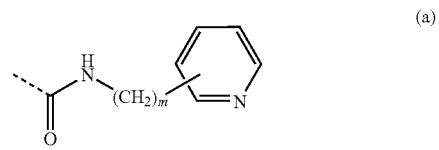

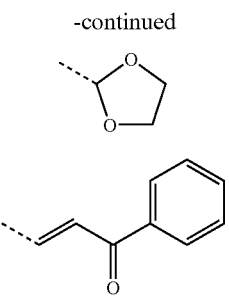

where n is an integer from 1 to 6;
where $R^3$ is straight or branched chain $C_1$-$C_8$ alkyl, $C_2$-$C_6$ alkenyl or $C_2$-$C_8$ alkynyl, aryl or heteroaryl group, optionally substituted with one or more substituents selected from halogen, $NH_2$, $NHR^4$, $N(R^4)_2$, OH, $OR^4$, acyl or phosphate; and where $R^4$ is a straight or branched chain $C_1$-$C_8$ alkyl group, or where two $R^4$ groups together form a cyclopentyl, cyclohexyl, morpholyl, or N-methylpiperazinyl substituent;
with ═══ indicates a single bond or a double bond;
provided that the following compounds are excluded:
3,4-dihydro-2H-naphtho[2,3-b]-1,4-thiazine-5,10-dione;
2,3-dihydro-7-methyl-1H-pyrido[3,2-g][3,2-g][1,4][1,4)benzothiazine-5,10-dione;
2,3-dihydro-1H-pyrido[3,2-g][1,4]benzothlazine-5,10-dione;
3,4-dihydro-8-(4-methyl-3-pentenyl)-1,1-dioxide-2H-naphtho[2,3-b]-1, 4-thiazine- 5,10-dione;
3,4-dihydro-7-(4-methyl-3-pentenyl)-1,1-dioxide-2H-naphtho[2,3-b]-1, 4-thiazine- 5,10-dione;
3,4-dihydro-1,1-dioxide-2H-naphtho[2,3-b]-1,4-thiazine-5,10-dione;
or:
a pure compound of formula (II)

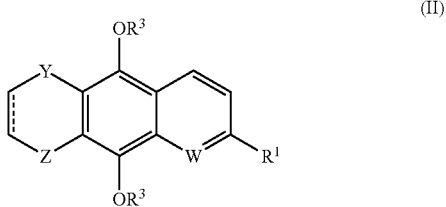

(II)

where: W, Y, Z and $R^1$ are as defined above;
$R^5$ is H, $C_1$-$C_6$ alkyl or acyl; and
═══ indicates a single bond or a double bond;
or a pharmaceutically acceptable salt thereof.

2. A compound as claimed in claim 1 which is a compound of formula (I).

3. A compound as claimed in claim 1 which is a compound of formula (II).

4. A compound as claimed in claim 1 where $R^1$ is straight or branched chain $C_1$-$C_8$ alkyl, $CO_2H$, $CO_2R^3$, CHO, CN, CON$(R^3)_2$, COH$(OR^3)$, H, or a radical of formula (a), (b) or (c).

5. A compound as claimed in claim 4 where $R^1$ is straight or branched chain $C_1$-$C_8$ alkyl, $CO_2H$, $CO_2R^3$, CN or CON$(R^3)_2$.

6. A compound as claimed in claim 5 where $R^1$ is straight or branched chain $C_1$-$C_8$ alkyl.

7. A compound as claimed in claim 6 where $R^1$ is methyl.

8. A compound as claimed in claim 6 where $R^1$ is substituted with one or more $N(R^4)_2$ substituents where the two $R^4$ groups together form a morpholyl substituent.

9. A compound as claimed in claim 5 where $R^1$ is CON$(R^3)_2$.

10. A compound as claimed in claim 9 where $R^3$ is methyl.

11. A compound as claimed in claim 5 where $R^1$ is $CO_2R^3$.

12. A compound as claimed in claim 11 where $R^3$ is straight or branched chain $C_1$-$C_8$ alkyl.

13. A compound as claimed in claim 12 where $R^3$ is methyl.

14. A compound as claimed in claim 5 where $R^1$ is $CO_2H$.

15. A compound as claimed in claim 5 where $R^1$ is CN.

16. A compound as claimed in claim 1 where Y is NH or $NR^2$ and Z is SO or $SO_2$.

17. A compound as claimed in claim 16 where Y is NH and Z is $SO_2$.

18. A compound as claimed in claim 1 where Z is NH or $NR^2$ and Y is S, SO or $SO_2$.

19. A compound as claimed in claim 18 where Z is NH and Y is $SO_2$.

20. A compound as claimed in claim 1 where the compound is a compound of formula (I) and where $R^1$ is $CO_2H$ or $CO_2R^3$ and Y is S, SO or $SO_2$.

21. A compound as claimed in claim 1 where the compound is a compound of formula (II) and where $R^5$ is H.

22. A compound as claimed in claim 1 where the compound is a compound of formula (I) and where $R^1$ is straight or branched chain $C_1$-$C_8$ alkyl or CO$(NR^3)_2$.

23. A compound as claimed in claim 22 where $R^1$ is methyl.

24. A compound as claimed in claim 22 where $R^3$ is methyl.

25. A pharmaceutical composition comprising a pharmaceutically effective amount of a compound of claim 1.

26. A method of treating an inflammatory disease or disorder, comprising administering to a patient in need thereof a therapeutically effective amount of a compound as defined in claim 1, where the inflammmatory disease or disorder is an inflammatory disease of the joints, skin, or muscle, or the inflammatory disease or condition is gout, acute or chronic idiopathic inflammatory arthritis, psoriasis, chronic dermatosis, myositis, a demyelinating disease, chronic obstructive pulmonary disease, interstitial lung disease, glomerulonephritis, interstitial nephritis, chronic active hepatitis, Croh's disease, ulcerative colitis, plaque formation in atherosclerosis, or multiple sclerosis.

27. A compound as claimed in claim 1, selected from:

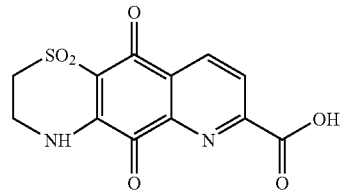

(1)

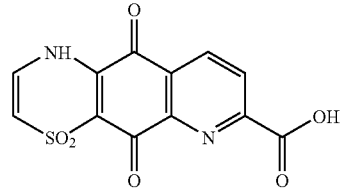

(2)

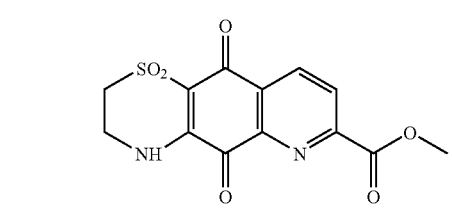
(3)
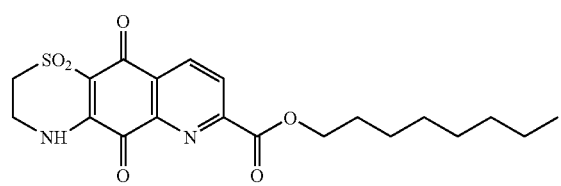
(4)
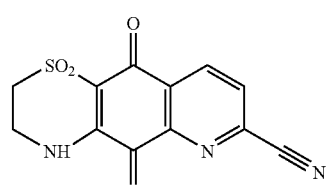
(5)
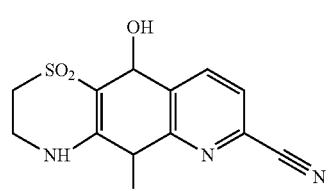
(6)
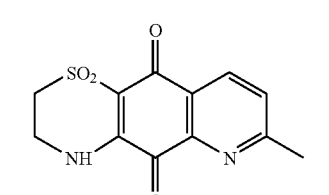
(9)
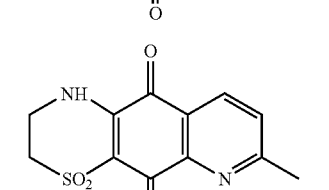
(10)
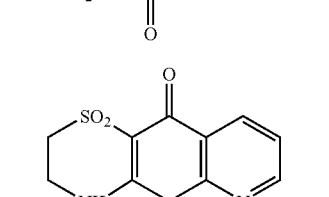
(11)
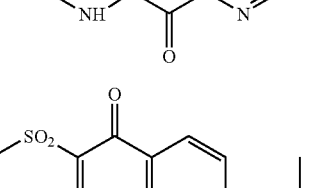
(12)
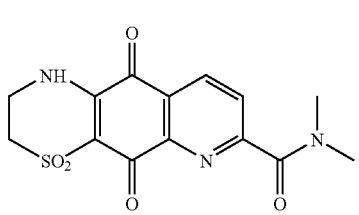
(13)
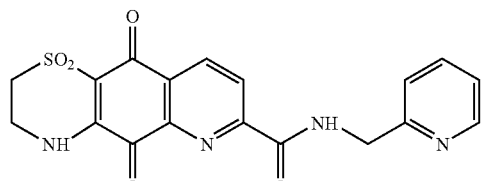
(14)
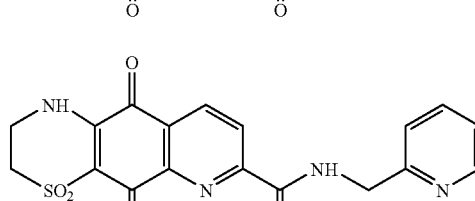
(15)
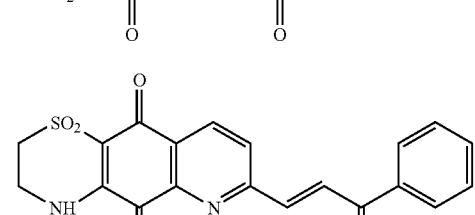
(16)
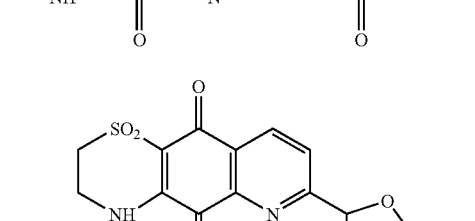
(17)
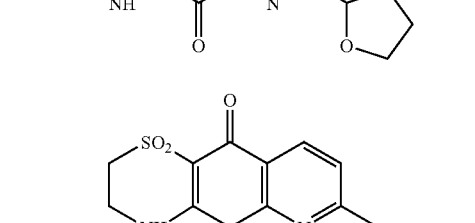
(18)
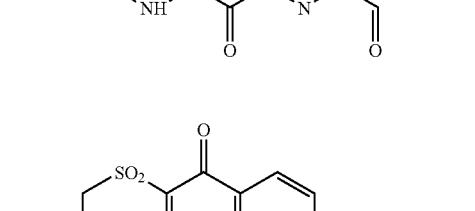
(19)
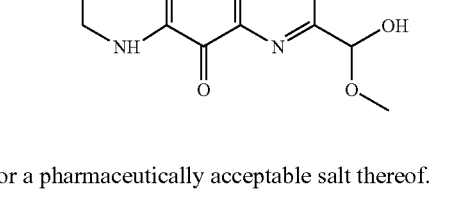
or a pharmaceutically acceptable salt thereof.
* * * * *